(12) United States Patent
Den Boer et al.

(10) Patent No.: US 6,896,171 B2
(45) Date of Patent: May 24, 2005

(54) EMAT WELD INSPECTION

(75) Inventors: Johannis Josephus Den Boer, Rijswijk (NL); Anthony Thomas Cole, Rijswijk (NL); Klisthenis Dimitriadis, Rijswijk (NL); Dirk Arie Kronemeijer, Rijswijk (NL); Jan Erik Vollebregt, Rijswijk (NL)

(73) Assignee: Shell Oil Company, Houston, TX (US)

( * ) Notice: Subject to any disclaimer, the term of this patent is extended or adjusted under 35 U.S.C. 154(b) by 38 days.

(21) Appl. No.: 10/621,506

(22) Filed: Jul. 17, 2003

(65) Prior Publication Data

US 2004/0134970 A1 Jul. 15, 2004

(30) Foreign Application Priority Data

Jul. 17, 2002 (EP) .............................................. 02077914

(51) Int. Cl.⁷ ......................... B23K 31/12; G01N 29/04
(52) U.S. Cl. .......................... 228/103; 228/104; 73/588
(58) Field of Search ................................ 228/103, 104, 228/102, 8; 73/579, 588

(56) References Cited

U.S. PATENT DOCUMENTS

| | | |
|---|---|---|
| 2,719,207 A | 9/1955 | Moyer |
| 4,100,809 A * | 7/1978 | Bobrov et al. .................. 73/638 |
| 4,127,035 A | 11/1978 | Vasile |
| 4,184,374 A | 1/1980 | Thompson et al. |
| 4,289,030 A * | 9/1981 | Alers et al. ..................... 73/588 |
| 4,471,658 A | 9/1984 | Morimoto |
| 4,566,625 A | 1/1986 | Moe |
| 4,593,568 A * | 6/1986 | Telford et al. .................. 73/623 |
| 4,669,650 A | 6/1987 | Moe |
| 4,685,334 A * | 8/1987 | Latimer ......................... 73/599 |
| 4,728,760 A | 3/1988 | Brolin et al. |
| 4,736,084 A | 4/1988 | Moe |
| 5,085,082 A | 2/1992 | Cantor et al. |
| 5,439,157 A | 8/1995 | Geier et al. ..................... 228/9 |
| 5,474,225 A | 12/1995 | Geier et al. ................... 228/104 |
| 5,526,691 A * | 6/1996 | Latimer et al. ................ 73/592 |
| 5,537,876 A * | 7/1996 | Davidson et al. .............. 73/624 |
| 5,549,003 A * | 8/1996 | Drescher-Krasicka ........ 73/606 |
| 5,581,037 A | 12/1996 | Kwun et al. |
| 5,619,423 A * | 4/1997 | Scrantz ......................... 702/51 |
| 5,652,389 A | 7/1997 | Schaps et al. ................. 73/643 |
| 5,721,413 A | 2/1998 | Moe |
| 5,760,307 A * | 6/1998 | Latimer et al. ................ 73/643 |
| 5,808,202 A | 9/1998 | Passarelli, Jr. ................ 73/643 |
| 5,924,745 A | 7/1999 | Campbell |
| 6,170,336 B1 | 1/2001 | Johnson et al. |
| 6,250,163 B1 * | 6/2001 | MacLauchlan et al. ....... 73/643 |

(Continued)

FOREIGN PATENT DOCUMENTS

| | | |
|---|---|---|
| EP | 0781994 A2 | 2/1997 |
| JP | 04265853 | 9/1992 |
| WO | PCT/US95/04232 | 1/1996 |
| WO | 98/33619 | 6/1998 |
| WO | 02/30611 A1 | 4/2002 |
| WO | 02/40986 A1 | 5/2002 |

OTHER PUBLICATIONS

Search Report dated Jul. 16, 2003.

*Primary Examiner*—Kiley S. Stoner

(57) ABSTRACT

A method for inspecting welds between welded tubular ends includes arranging a series electromagnetic acoustic transducer (EMAT) assemblies in circumferential direction adjacent to an inner and/or outer surface of at least one of the welded tubular ends and inducing the EMAT assemblies to transmit sequentially or simultaneously acoustic shear wave signals towards the weld and to detect the shear waves reflected by and/or passing through the weld while the EMAT assemblies are maintained in a substantially fixed position relative to the weld such that at least a substantial part of the weld is scanned by the EMAT assemblies instantly after the weld is made.

11 Claims, 17 Drawing Sheets

U.S. PATENT DOCUMENTS

| | | | |
|---|---|---|---|
| 6,568,271 B2 * | 5/2003 | Shah et al. | 73/599 |
| 6,597,997 B2 * | 7/2003 | Tingley | 702/34 |
| 6,624,628 B1 * | 9/2003 | Kim et al. | 324/240 |
| 6,751,560 B1 * | 6/2004 | Tingley et al. | 702/51 |
| 2003/0033870 A1 * | 2/2003 | Shah et al. | 73/299 |
| 2004/0091076 A1 * | 5/2004 | Kerr et al. | 376/260 |
| 2004/0093949 A1 * | 5/2004 | Alleyne | 73/625 |
| 2004/0134970 A1 * | 7/2004 | Den Boer et al. | 228/104 |

* cited by examiner

EMAT WELD INSPECTION

FIELD OF THE INVENTION

The invention relates to a method and system for inspecting welds by means of an Electro Magnetic Acoustic Transducer (EMAT) assembly.

BACKGROUND OF THE INVENTION

The use of EMAT assemblies for inspecting welds is known from U.S. Pat. Nos. 5,439,157 and 5,474,225. In the known EMAT weld inspection methods a robotic transport apparatus containing EMAT transmitting and receiving coils is automatically positioned at one side of a just-completed weld whereupon the EMAT transmitting coil transmits ultrasonic SH shear waves towards the weld and the EMAT receiving coil transduces any ultrasonic SH shear waves reflected by the weld in a signal which is used to signal the presence of defects in the weld on the basis of the received signal. The robotic transport apparatus is in use moved along the surface of one of the welded plates parallel to the weld and may be connected to a control unit which automatically adjusts the settings of the welding apparatus which moves ahead of the EMAT weld assembly. The use of a robotic transport apparatus is not practical for inspection of welds between tubulars since it requires the robotic transport apparatus to rotate around a welded tubular, which is time consuming and requires the use of a fragile robotic tool.

The use of EMAT devices for weld and/or pipe inspection is also disclosed in U.S. Pat. No. 5,652,389 to Barnes, et. al., U.S. Pat. No. 5,760,307 to Latimer et. al., WO Patent No. 02/40986 and U.S. Pat. No. 5,808,202 to Passarelli. Barnes discloses a pulse-echo technique and apparatus for inspection of inertia welds in plat-plates using EMAT. Latimer discloses a method to eliminate root and crown signals using crossed or collinear EMATs, and Passarelli discloses a pulse-echo technique for the inspection of cylindrical objects including rods and tubes.

The device disclosed by Passarelli has the disadvantage that it is has a fixed ring-shape construction, which cannot be put readily around the tubulars and the weld at the rig floor without the danger of damaging the device or at the expense of substantial time delays. Another disadvantage to this arrangement is the geometry of the electromagnets, the transmitter and the receiver coil, which does not provide a 100% inspection of the weld around the circumference of the pipe, as the aperture of the transmitters is smaller than the ultrasonic field at the weld region. Rotating the tubular could mitigate the disadvantage, but that is not possible when the tubulars are welded at the rig floor, as will be explained below. An additional, difficulty posed by this and other prior art is that the weld is inspected by pulse-echo reflection measurement only. However, to prevent miss-interpretation of the reflected signals, e.g. due to diffraction or scatter at the weld, it is preferred to measure both reflection and transmission at the same time using at least two EMATs positioned upstream and downstream from the weld.

SUMMARY OF THE INVENTION

The tubular weld inspection method according to the invention comprises arranging a series of electromagnetic acoustic transducer (EMAT) assemblies in circumferential direction adjacent to an inner and/or outer surface of at least one of the welded tubular ends and inducing the EMAT assemblies to transmit sequentially (ie. individually or grouped) or simultaneously acoustic shear wave signals in different modes and angles towards the weld and to detect the shear waves reflected by and/or passing through the weld such that at least a substantial part of the weld is scanned by the EMAT assemblies and wherein the EMAT assemblies are maintained at a substantially fixed position relative to the weld during the scanning operation.

Use of EMAT assemblies that are maintained at a substantially fixed position relative to the weld during the scanning operation enables instant weld inspection after the weld has been made and thus enables significantly faster weld inspection that with currently known EMAT inspection tools where the EMAT assemblies are moved relative to the weld during the weld scanning process as disclosed in U.S. Pat. No. 4,184,374; U.S. Pat. No. 5,085,082 and International patent application WO96/02831.

The EMAT assemblies may comprise a ring shaped assembly of circumferentially spaced EMAT transmitters and a ring shaped assembly of circumferentially spaced EMAT receivers, which is arranged between the weld and the ring shaped assembly of EMAT transmitters.

The EMAT assemblies may also comprise ring shaped assemblies of EMAT transmitter and receiver assemblies at both sides of the weld when seen in longitudinal direction of the welded tubulars.

The EMAT transmitter and receiver assemblies may include a matrix of EMAT transducers which at least partly overlap each other in a circumferential direction so that the entire length of the weld can be inspected instantly after the welding operation by a stationary array of EMAT transmitters which each transmit shear waves into a segment of the pipe wall that tends to be narrower that the width of the EMAT transmitter itself.

The EMAT transducers of at least one matrix may be stacked on top of each other in a radial direction relative to the tube wall. Alternatively, the EMAT transducers of at least one matrix are staggered in a substantially longitudinal direction relative to the tube wall.

In an embodiment the EMAT assembly is arranged on a carrier body, which is arranged in the interior of at least one of the welded tubulars. This embodiment of the EMAT assembly can also be used for inspection of welds in-situ, e.g. downhole, or in laying barge pipelines, either immediately after welding or some time later, e.g. to inspect the quality of the welds after several years service.

In an alternative embodiment the EMAT assembly is arranged on a carrier sleeve which surrounds at least one of the welded tubulars and which can optionally be split into at least two sleeve segments after completion of the welding operation. This embodiment can also be used for inspection of welds in-situ, e.g. at the rig floor or in laying barge pipelines.

The EMAT tubular weld inspection method and assembly is able to inspect the quality of forge welded tubulars instantly after the forge weld has been made.

The EMAT assembly according to the invention may include a series of electromagnetic acoustic transducers which are in use distributed in a circumferential direction adjacent to an inner and/or outer surface of at least one of the welded tubular ends and are configured to transmit sequentially or simultaneously acoustic shear wave signals in different modes and angles towards the weld and to detect the shear waves reflected by and/or passing through the weld such that at least a substantial part of the weld is scanned by the EMAT assembly.

In an embodiment, the assembly comprises at least two longitudinally spaced ring shaped arrays of EMAT transmitters and receivers such that the ring shaped arrays of EMAT receivers are located between the ring shaped arrays of EMAT transmitters.

DETAILED DESCRIPTION OF THE INVENTION

Figure 1:
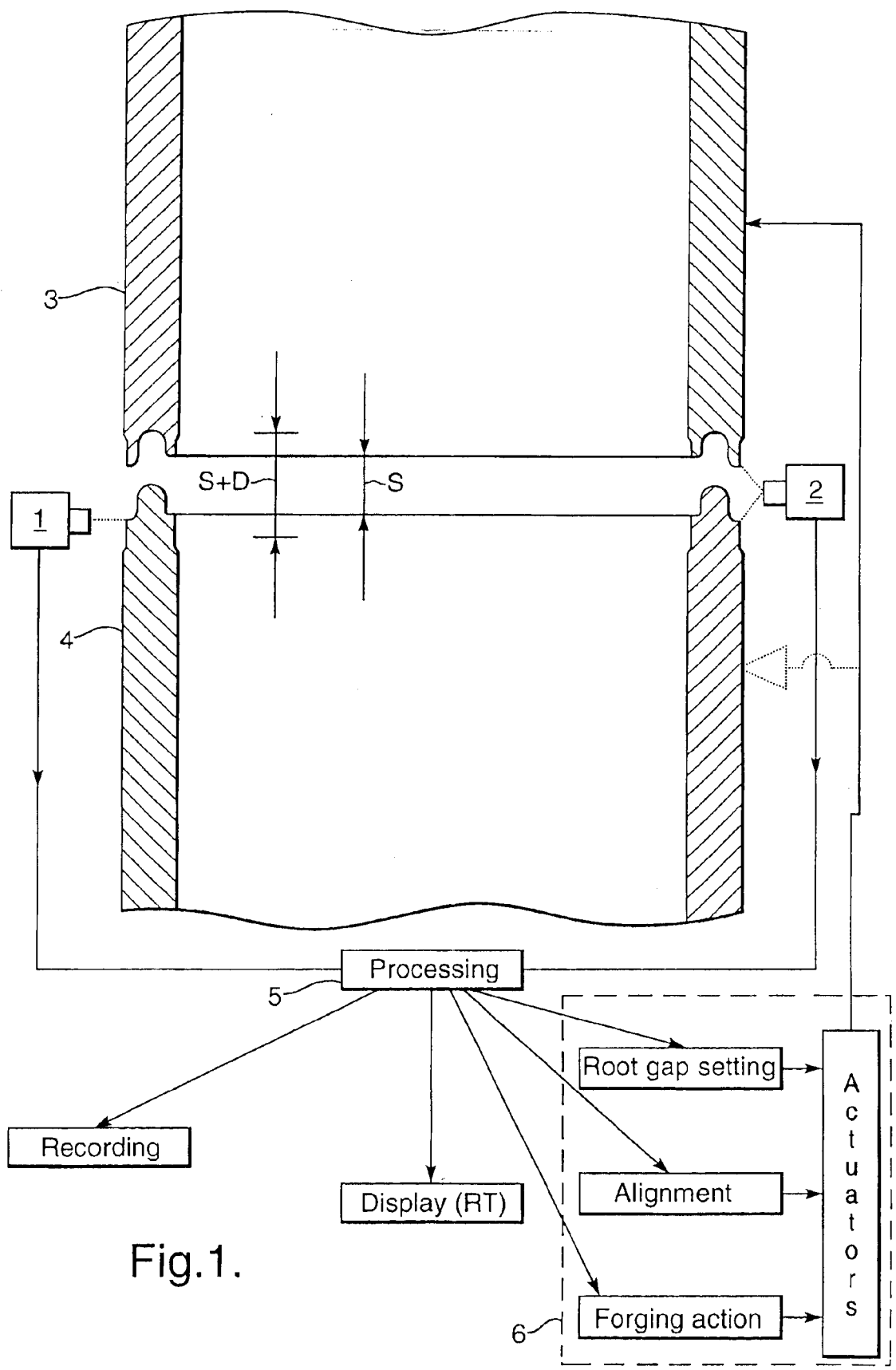
FIG. 1 depicts a schematic outline of an assembly for carrying out the automated forge welding method according to the invention.

As shown in FIG. 1 the positions of the tubular ends 3 and 4 that are to be forge welded together are monitored by cameras 1 and 2 which are coupled to a camera signal processor 5 which automatically controls a gripping assembly 6, such that the spacing S between the heated tubular ends 3A and 4A is well defined during the heat up phase and the tubular ends are moved towards each other when a pyrometric control unit indicates that the tubular ends have reached a predetermined minimum and/or maximum temperature along at least a substantial part of the circumference thereof, whereupon the gripping assembly is activated to move the tubular ends 3A and 4A towards each other over a predetermined distance (S+D) which exceeds said spacing (S) with an additional distance (D) of less than a few millimeters, such that a forge weld is obtained of a substantially equal and high quality over the entire circumference of the forge welded ends and only minimal external and/or internal upsets of the forge welded ends 3A, 4A is created, which upsets do not have to be removed afterwards by grinding, milling or machining.

Figure 2:
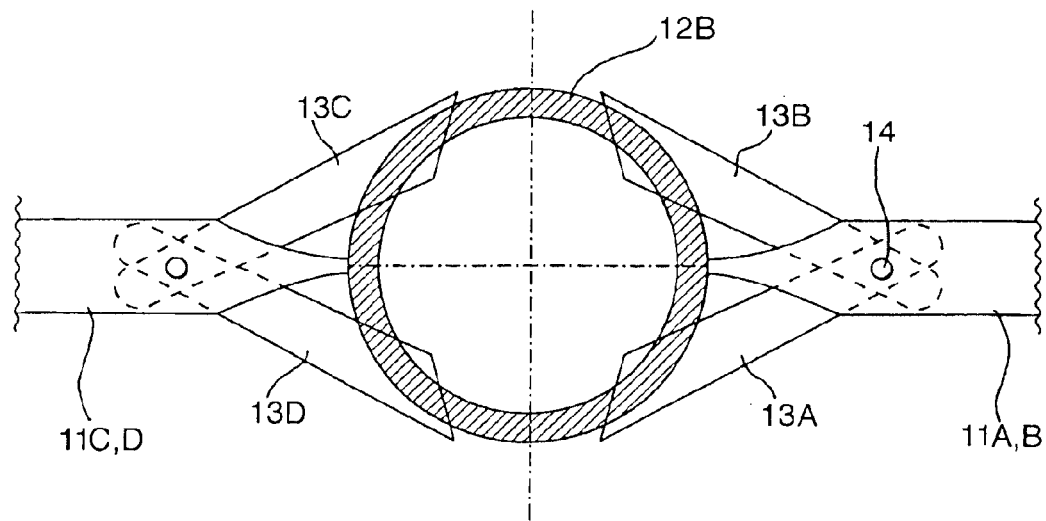
FIG. 2 depicts a longitudinal sectional view of an automated forge welding assembly according to the invention which is equipped with spacer elements for maintaining the tubular ends at a predetermined spacing during the heat up phase.
Figure 3:
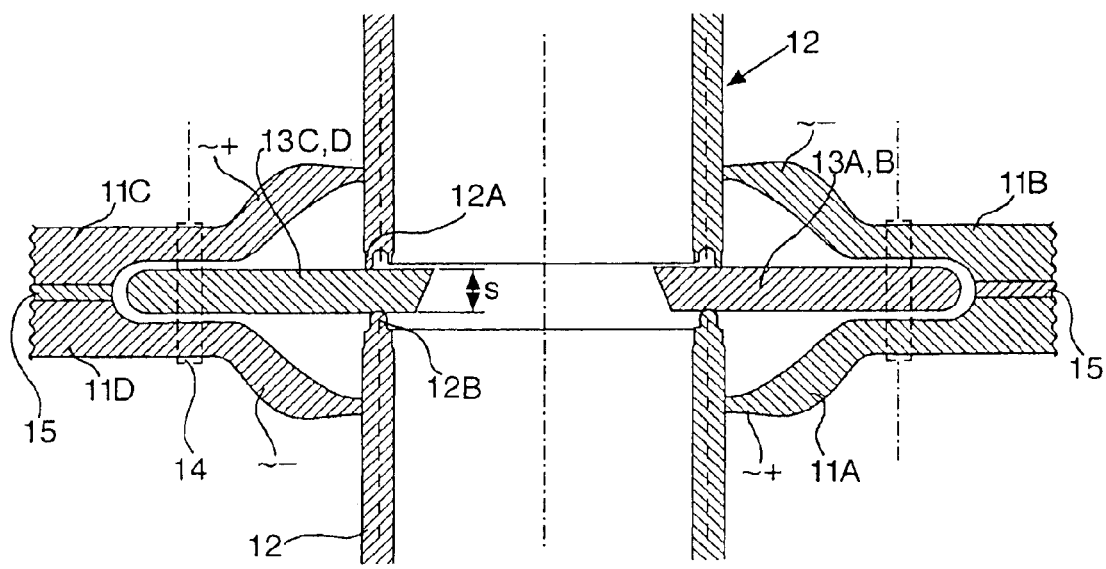
FIG. 3 is a cross-sectional view of the forge welding assembly of FIG. 2.

Referring to FIGS. 2 and 3 there is shown a forge welding assembly in which a set of two pairs electrodes 11A–D transmit high frequency electrical current through the walls of a pair of pipes 12 the ends 12a, 12b of which are held at a predetermined spacing S by a set of four spacing elements 13A–D. The electrode pairs 11A–B and 11C–D at each side of the pipes 12 are electrically insulated from each other by an electrical insulation layer 15. The spacing elements 13A–D are secured to the electrodes 11 by electrically insulating pivots 14 and each spacing element 13A–D comprises a heat resistant electrically insulating head, which is suitably made of a ceramic material.

The spacing elements 13A–D may be provided with pyrometric and/or compression sensitive sensors which are able to detect the temperature of each pipe end 12A–B during the heat up phase and also the location of the pipe end 12A–B relative to the spacing element 3 and the compressive force applied by the pipe ends 12A–B to the spacing element 13. The compression sensitive sensors may comprise piezoelectric elements which are located close to the pipe ends 12A, 12B or at a selected distance therefrom such that the time difference between the transmitted and reflected vibrations is used to assess the contact point(s) and compression forces between the spacing elements 13A–D and the pipe ends 12A, 12B.

The sensors may be coupled to a welding control assembly as shown in FIG. 1 which pulls out the spacing elements 13 from the spacing if the pipe ends 12A,B have reached a selected temperature which may be below or substantially equal to the temperature required for forge welding. The spacing elements 13A–D may furthermore be equipped with channels through which a reducing non-explosive shield gas is injected towards the heated pipe ends. The non-explosive shield gas suitably comprises more than 90% by volume of nitrogen and more than 2% by volume of hydrogen.

Accurate positioning of the tubular ends relative to each other during the heat-up and forge welding operation is important to obtain a high welding quality and minimal upsets in the welding zone.

It may be beneficial to provide the tubular ends with locking and orienting grooves that fit into profiled gripping arms of the automated forge welding tool.

Figure 4:
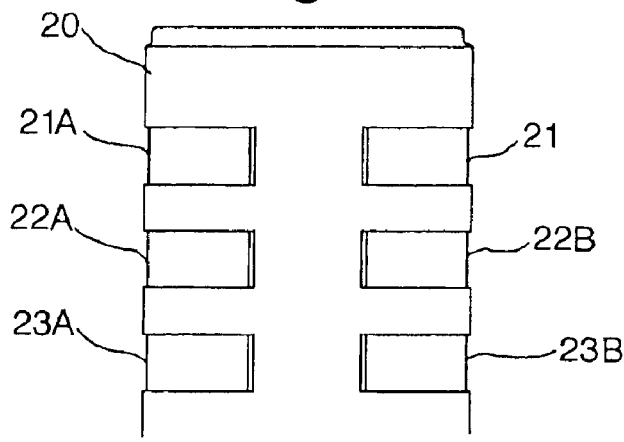
FIG. 4 is a side view of a tubular end, which is provided with a series of locking and orienting grooves.
Figure 5:
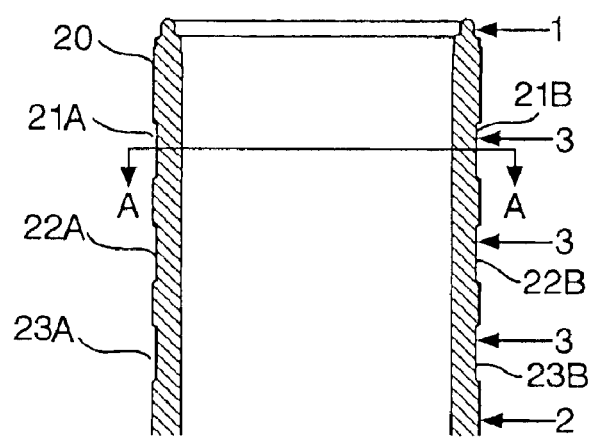
FIG. 5 is a longitudinal sectional view of the tubular end of FIG. 4.
Figure 6:
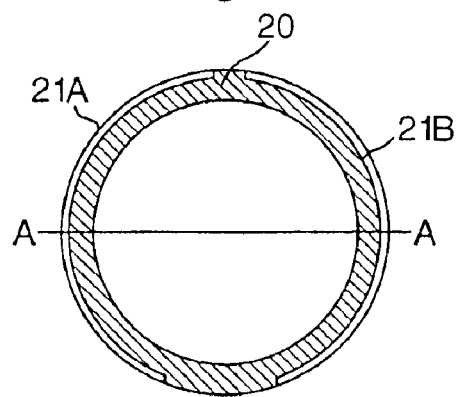
FIG. 6 is a cross-sectional view of the tubular end shown in FIGS. 4 and 5 taken across line A—A and seen in the direction of the arrows.

FIGS. 4, 5 and 6 show a tubular end 20 that is provided with three pairs of semi-circular grooves 21–23A–B. The automated welding tool may be equipped with semi-circular gripping arms which have profiles and/or balls that fit into the semi-circular grooves 21–23A–B such that the risk of slipping of the tubular end 20 through the gripping arms is minimized, even if a tubular string of several kilometers long is suspended into a well from the tubular end 20.

The method according to the invention may be employed to join tubular sections by forge welding to a tubular string of any length. The tubular string may be a string of oilfield tubulars, such as an oil and/or gas well casing, a production tubing that is suspended in an oil and/or gas well, a vertical or catenary steel riser extending between an offshore platform deck and the seabed, a tubular leg of an offshore structure, a tubular tensioned leg, known as a tendon, of a floating tension leg platform, or a subsea or an onshore underground or above-ground pipeline for transport of fluids.

During the heat-up and forge welding operation the interior of the tubular ends that are to be joined may be sealed off from other parts of the interior of the tubular string by inserting a mandrel or spear into the interior of the tubulars in the welding zone, which mandrel or spear may be provided with expandable sealing rings, shield gas injection means and/or weld inspection means, such as electromagnetic acoustic transducers, known as EMAT weld inspection equipment. Alternatively the interior of the tubulars adjacent to the welding zone may be sealed off during the forge welding operation by injecting an expanding rigid foam, such as polyurethane foam, into the tubulars, which foam is removed from the interior of the tubulars after the forge welding operation.

The tubular ends that are to be joined by forge welding may be machined into complementary concave and convex shapes in a pipe manufacturing plant or by a machining tool at or near the automated forge welding tool.

The tubular ends may be protected during transport from the manufacturing plant to the forge welding site by metal or plastic caps that may be equipped with expandable gripping profiles or balls that may fit into the locking grooves shown in FIGS. 4, 5 and 6.

The automated forge welding device according to the invention may be combined with a pipe manipulation device on an oil and/or gas drilling or production rig which is known as the iron roughneck. The pipe manipulation device may be equipped with gripping arms and/or low-scarring dies and/or balls which grab the tubulars internally and/or externally.

The traditional method of connecting lengths of OCTG (Oil Country Tubular Goods), whether they are for downhole casing or tubing, is to use a threaded connection or another form of joining based on a suitable welding technique like explosive welding, shielded active gas welding, flash butt welding, etc.

In the case of welding, the presence of certain defects will reduce the strength and thus the structural integrity of the downhole oil or gas tubular. Therefore, proper inspection of the weld-for flaws or other irregularities is desirable. It is preferred to inspect the weld immediately after the weld is made using a non-destructive test technique.

Figure 7A:
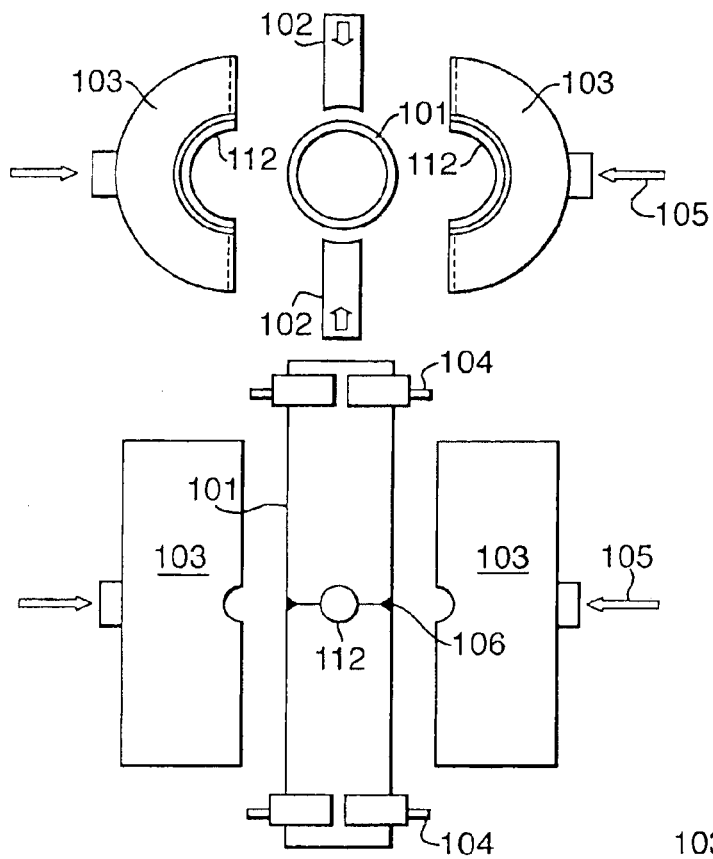
FIGS. 7a and 7b show side and top views of a forge welding apparatus which is equipped with an EMAT weld inspection assembly according to the invention.
Figure 7B:
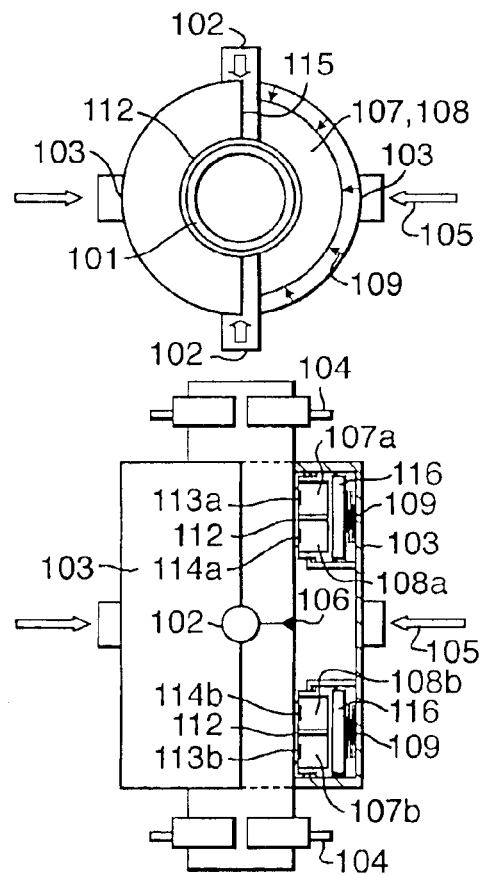
Figure 8:
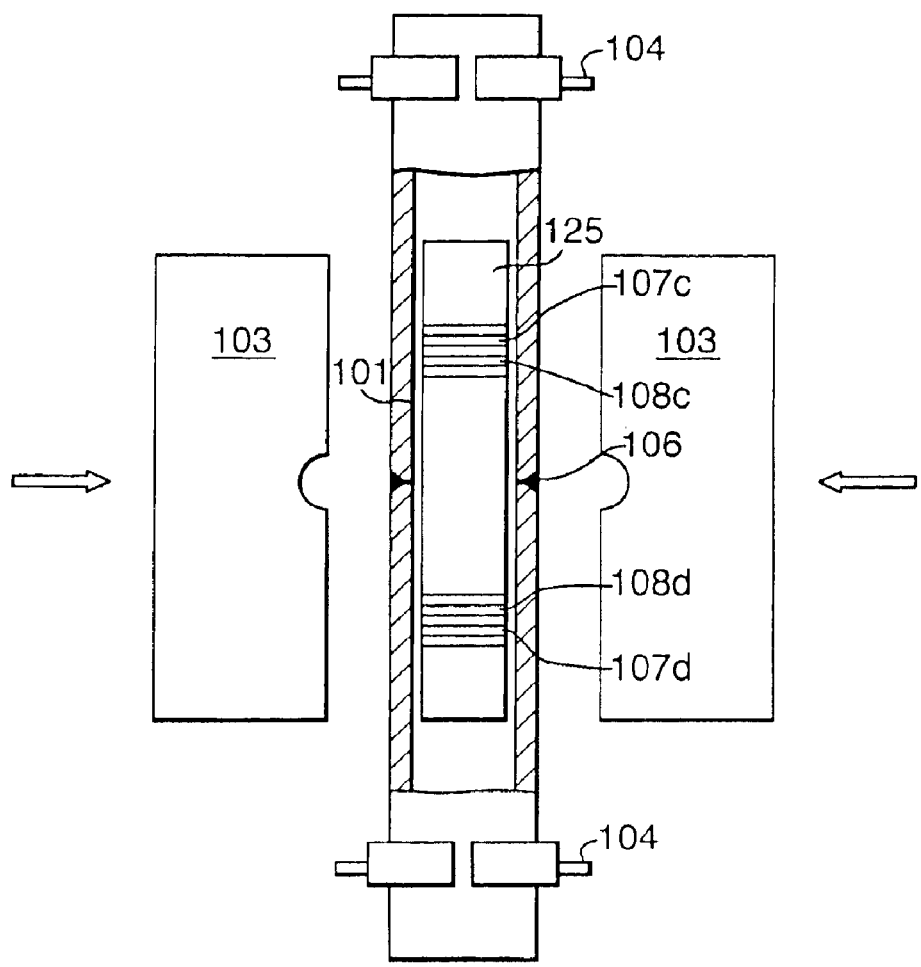
FIG. 8 shows a longitudinal section view of a spear which is inserted into a pair of forge welded tubulars and which carries ring shaped assemblies of EMAT transmitters and receivers at each side of the weld.
Figure 9:
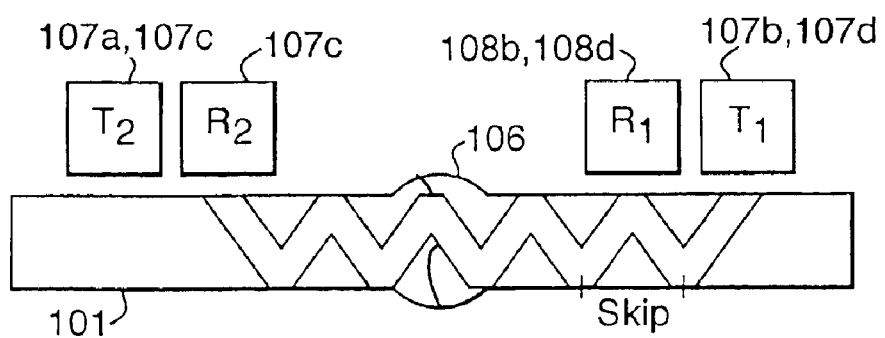
FIG. 9 shows a longitudinal sectional view of a weld between tubulars through which an ultrasonic signal is transmitted.

Referring now to FIGS. 7 and 8, at the rig-floor the tubulars 101 may be kept aligned in an upright and fixed position during welding using pipe grippers 104. After inspection and approval of the weld quality the tubular 101 is lowered in to the wellbore, and another piece of tubing or casing (minimal length preferably about 10 meters) is positioned on top of it and welded, etc. To minimise the loss of rig-time and to enhance safety at the rig-floor, it is preferred to perform the inspection of the weld in a fully automatic way, starting immediately after the weld is made and completed in a minimum of time. For well integrity reasons it is preferable to inspect the weld over its full length along the circumference of the pipe.

At present, a range of well known technologies are available for inspection of butt welds in tubes and pipes, based on x-ray, ultrasonic inspection techniques, EMAT, eddy current inspection and their derivite techniques as SLOFEC, remote field eddy current, partial saturated eddy current, etc.

Inspection of tubulars intended for use in downhole environments presents challenges that disqualify many techniques and/or configurations. These challenges include a desire for:

a. rapid completion of testing on relatively poorly prepared surfaces, with the weld still hot.
   b. fully automatic operation of the testing equipment.
   c. immediate feedback to allow assessment for acceptance or rejection of the weld.
   d. integration with the welding device
   e. safe operation in a potentially hazardous environment.

Some embodiments of the present invention enable the use of EMAT weld inspection technology at the rig-floor.

EMAT (electromagnetic acoustic transducer) inspection is a known inspection technique, in which interaction between a magnetic and electromagnetic field induces acoustic energy in the test piece. The generated acoustic wave is reflected by anomalies or defects and can be detected by a suitable receiver. The receiver can be either a conventional piezo-electric transducer or an EMAT. To validate the magnetic coupling of the transmitting EMAT a receiver on the other side of the weld can be applied as a transmission check.

In this case the relative strength of this energy is altered by the presence of defects and is used to identify defects.

Transmission and receiver EMAT assemblies may be used which are maintained in a stationary position relative to the weld and are suited to inspection of forge-welded pipes instantly after the forge welding operation. To ensure correct and accurate positioning of the EMAT probes, a novel design has been made where stationary EMAT assemblies are configured to scan the entire length of the weld that allows integration into the forge-welding machine or into the internal spear used for the alignment of the tubulars while welded together.

The external non-destructive weld testing apparatus shown in FIGS. 7 and 8 include two EMAT probes 107, 108. The EMAT probes 107, 108 may be positioned either above the weld 106, below the weld 106 or, preferably, above and below the weld 106 and that they are in close proximity (typically no more than 2 mm from) the pipe wall. Each EMAT probe comprises a series of circumferentially distributed EMAT transmitter and receiver assemblies 107a, 107b, 108a, 108b. In each assembly the receiver 108a, 108b is positioned adjacent to the transmitter 107a, 107b but between the transmitter 108a, 108b and the weld 106. The stationary EMAT probes can be integrated into the external gas shield chamber 103 of the forge-welding machine (FIG. 7) or into the internal spear 125 (FIG. 8).

The stationary EMAT probe 107, 108 is ring-shaped as shown in FIGS. 7a and 7b and is segmented into at least two parts as illustrated in FIG. 7a. During the whole welding and inspection operation, the pipes 101 are kept in a fixed position, they cannot rotate, using pipe grippers 104. The gas shield chamber 103 of the forge-welding machine is closed during that time and surrounds the electrodes 102 that are pressed against the pipes 101 before the forge operation to heat the pipe ends that are to be forge welded together.

Control electronics, pre-amplifiers, signal pre-processors etc. may be located close to the electromagnets and the EMAT transmitter and receiver coils T/R in printed circuits 116. Active cooling for the electromagnets is also provided by flushing shield gas into the chamber 103, as illustrated by arrows 105.

In use, each R/T pair 108a, 107a, 108b, 107b may be activated and controlled by an electronic switch box in printed circuit 116. A signal may be generated by each of the transmitters 107a, 107b, etc. and transmitted via the pipe 101 toward the weld 106, the adjacent receiver 108 detects this signal for calibration purposes and the signal continues to propagate toward the weld 106. If there is a defect in the weld 106 then the signal is reflected back toward the transmitter 107a, 107b whereupon the receiver 108a, 108b will detect it and report a defect.

When applied together with the forge-welding machine as illustrated in FIGS. 7a and b the EMAT probes 107, 108 are automatically centred around the pipe wall 101, using a spring system 109, when the gas shield chamber 103 may be closed. The surfaces 113a–b, 114a–b of the EMAT transmitters and receivers 107a–b, 108a–b are protected by a thin film 112, typically a 0.1 mm metal thick metal film although other wear resistant materials can be employed.

FIG. 8 depicts EMAT probes which are mounted on an internal spear 125 for e.g. forge welding. In this embodiment the EMAT inspection probes 107, 108 comprise a series of circumferentially spaced pairs of EMAT transmitters 107c and 107d and EMAT receivers 108c, 108d at each side of the weld 106. Provision is made in the spear 125 for the permanent or electromagnets required for EMAT inspection and a suitable power supply, electronic switching box and data umbilical may be provided.

In one embodiment, the spear 125 is pre-positioned in one of the pipes 101 to be welded. This allows inspection probes to be in good contact with the pipe wall without a drift requirement and can be accomplished by using a simple backing material such as a foam rubber. Where the inspection device needs to be drifted into position then the EMAT probe assemblies 107c–d, 108c–d are positioned against the pipe 101 using an activation method of which there are several possibilities.

The EMAT probe assemblies 107, 108 are stand-by during the welding operation and start the inspection immediately after the welding process is completed and the local temperature of the weld is low enough, e.g. 700° C.

An almost identical configuration can be used in a pipe inspection pig or logging device for inspection of welds in-situ, e.g. downhole or in pipelines at or near the earth surface to inspect the quality of the welds after several years service.

FIG. 8 illustrates the benefits of the use of a second series of EMAT receivers e.g. R2 on the opposite side of the weld 106 to the transmitters, e.g. T1 in addition to the conventional use of a first series of EMAT receivers R1 at the same side of the weld 106 as the transmitters T1. In the event that there is no defect present in the weld 106 this second series of matching receivers R2 will detect a strong signal when the signal has passed through the weld. If this second series of receivers R2 is not present then a larger degree of uncertainty exists with regard to defect sizing because reflected signals may scatter and be lost, in which case the size of a defect in the weld 106 may be incorrectly/misleadingly reported.

Besides validation, the symmetrical configuration of transmitters and receivers T1,2 and R1,2 at both sides of the weld 106 provides means for gain control of the receiving coil e.g. R1. A further advantage of the symmetrical transmitter and receiver configuration T1,2 and R1,2 is that it enables the EMAT system to be operated in different modes. For example, by altering the relative angle between the pipe, magnetic and electromagnetic field it is possible to cause the steel to vibrate in just any direction. One of the advantages of this is that it allows the full body of the pipe wall to be "vibrated" and for the full body vibration to travel along the pipe parallel to the pipe wall. This prevents skipping as indicated in FIG. 8 and improves the signal-to-noise-ratio significantly. The same process is repeated for transmitter T2 thus giving redundancy to the entire configuration.

Figure 10A:
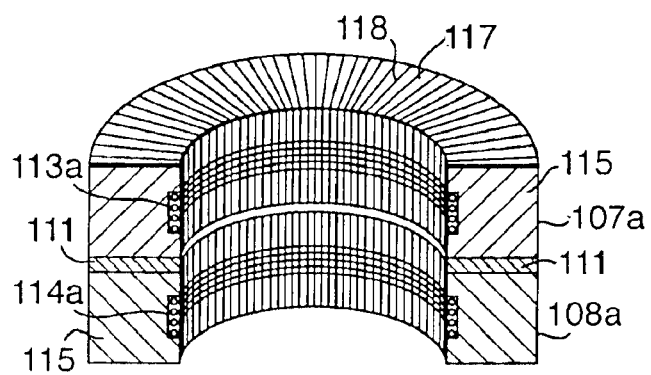
FIGS. 10a–e show a three-dimensional view of an EMAT transmitter and receiver assembly and how the acoustic signal is transmitted into the tubular wall.
Figure 10B:
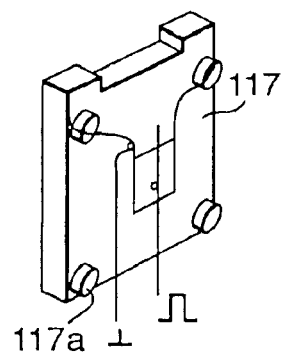

Reference is made to FIGS. 10a and b, which depict EMAT transducer and receiver probes 107, 108 that are composed of a set of laminated electromagnets 117, which may be controlled individually in groups or all at the same time. The individual electromagnets 117 are separated form each other by a thin spacer 118. In the preferred embodiment illustrated in FIG. 10b the individual electromagnets 117 can be put together with legoland type connections 117a. This construction enables the EMAT probe assemblies 107, 108 to be re-configured for different pipe diameters. The ends of the EMAT probes 107, 108 are covered with a suitable face protection material 115, e.g. Vespel, to prevent damaging and fouling of the transducer and receiver assemblies. At this location (on both sides) the flexible transducer and receiver coils 113a, 114a can move freely to adapt to diameter changes. The EMAT probe assemblies 107, 108 are separated by means of another dielectric spacer 111. The transducer and receiver coils 113a, 114a are placed inside a recessed area or at the surface of the electromagnet elements.

Figure 10C:
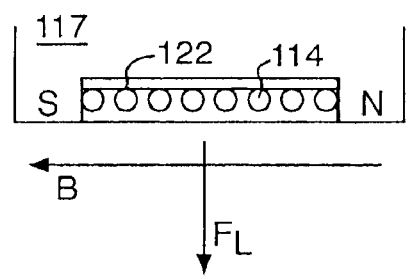

Reference is made to FIG. 10c. An electrostatic shield 122 is used to safeguard the EMAT receiver coil 114 from the effects of undesirable electric interference. The electrostatic shield, e.g. mu-metal, grounded, acts as a barrier to protect the EMAT receiver coil 114 from electrostatic interference and radio frequency interference. (EMI/RFI).

Figure 10D:
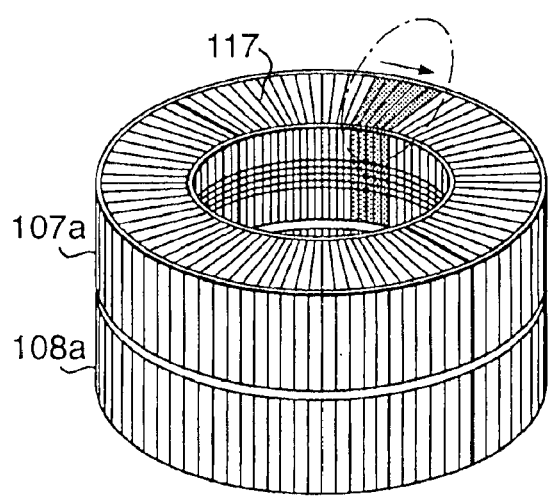
Figure 10E:
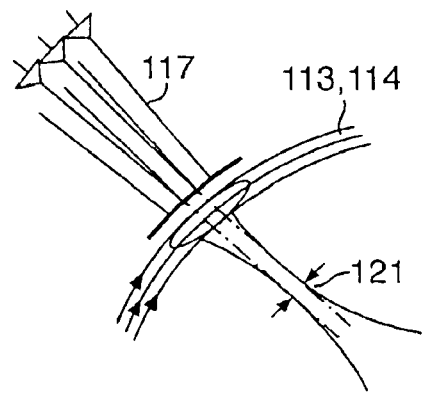

Reference is made to FIGS. 10d and 10e. Here the means are disclosed by whom to create a focal area (aperture) of the ultrasonic wave 121 that has an identical size as one or more of the electromagnet elements 117. One or more (could even be all) electromagnet elements 117 can be magnetised thus forming a larger magnetic field than from one single electromagnet element 117. The electromagnet elements 117 can be switched on and off individually, in groups or all at the same time, using the control electronics in an electric current 116 as illustrated in FIG. 7.

Reference is made to FIG. 11. Using novel design, use and control of meander-loop coils elements 123 provide the option to select different modes of operation and transmission angles of the ultrasonic wave, allowing a full inspection of the entire weld all around the circumference of the pipe.

Figure 11A:
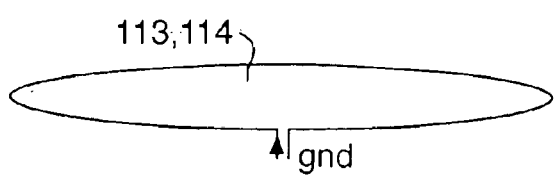
FIG. 11 shows various suitable configurations of the EMAT transmitter and receiver assemblies.
Figure 11B:
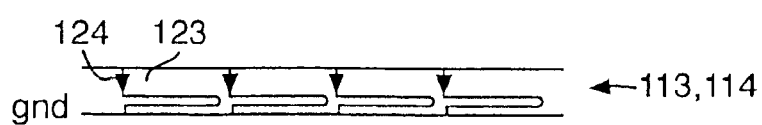
Figure 11C:
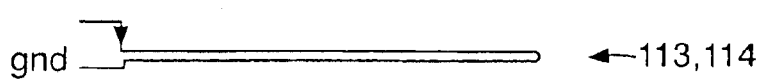
Figure 11D:
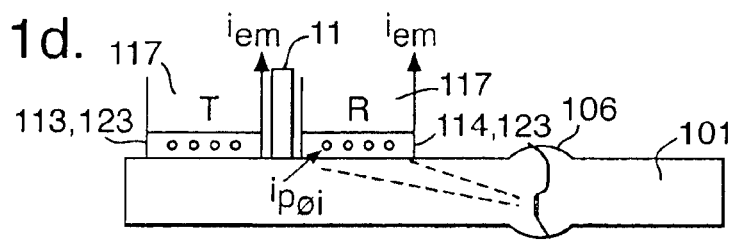
Figure 11E:

Within the ring of electromagnets a transmitting or receiving coil 113, 114 is present as illustrated in FIG. 11a, which can be a length of wire or build up out of separate meander-loop coil elements as illustrated in FIG. 11b. The transmitting or receiving coil elements 113, 114 can be controlled separately to obtain either one large meander-loop as shown in FIG. 11c or a phased array to generate an angled ultrasonic wave as shown in FIG. 11d. The receiver coil elements 123 are equipped with suitable pre-amplifiers 124. They can be processed separately or combined using the control electronics in 116.

Furthermore, by introducing small coil elements 123 a number of additional different configurations illustrated in FIGS. 11e, 11f, 11g, 11h can be created for different inspection purposes.

Figure 11F:
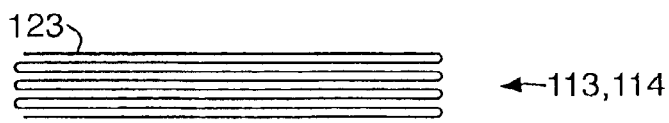
Figure 11G:

Basic configurations are:

(I) a long meander loop coil (i.e. circumferential direction) as illustrated in FIG. 11f, (II) a short meander loop coil (i.e. radial direction) using a single layer of coils as illustrated in FIG. 11g.

Figure 11H:
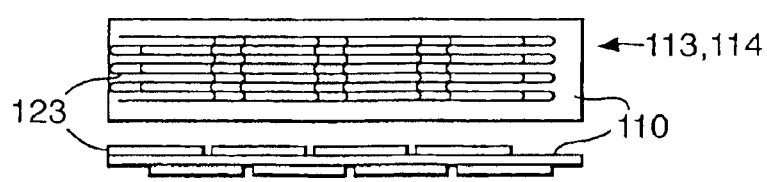

(III) two or more staggered layers as illustrated in FIG. 11h of can be used to create an improved coverage, additional-depth direction and better signal-to-noise ratio. The overall thickness of the staggered layers should be small, in the order of 1 mm.

Variations are possible.

An embodiment includes sandwiching two or more layers of flexible probe around the full circumference of the pipe. An alternative embodiment would have the layers of EMAT probes positioned in a similar staggered pattern but with one layer above the other. The transmitter and receiver coils may be put on a flexible carrier or substrate, which can be exchanged readily at the rig-floor.

An embodiment of the present invention includes shaping the tubular ends that are to be welded together into a sloping configuration such that when the tubular ends are heated during the forge welding process the heated tubular ends deform as a result of thermal expansion into a substantially longitudinally oriented cylindrical shape.

In addition the portion of each pipe that is to be forged may be reduced in cross section such that deformation during forging returns it to a dimension substantially the same as its original thickness.

The precise angles and dimensions of-the end preparation depend on the material being joined and its coefficient(s) of expansion, wall thickness, pipe diameter, degree of heat required for welding, the width of the heated zone and the desired forge length. Typical values are provided in Table 1 below for carbon steel tubes approximately 4 mm wall thickness and 70 mm diameter.

The sloping angle of the inner and/or outer walls of the tubular ends may be selected such that the ratio between the average diameter $D(t)$ of the tip of the tubular end and the average diameter $D(b)$ of the base of the tubular end is related to an estimated temperature difference between said tip and base of the tubular end during the forge welding process and a thermal expansion co-efficient of the steel grade(s) of the tubular end.

For many forge welding operations said ratio $D(t)/D(b)$ may be selected between 0.8 and 0.99.

To increase the surface of the forge welded pipe ends and to simultaneously assist alignment of the pipe ends the end face of one of the tubular ends that are to be welded together may a substantially convex shape and the end face of the other tubular end may have a substantially concave shape.

The forge welded tubulars may comprise a low grade steel base pipe and a higher grade steel cladding on the inner and/or outer surface of the base pipe. In such case it is preferred that the end faces are shaped such that when the tubular ends are pressed together the end faces of the cladding(s) touch each other first the end faces of the base pipe ends subsequently touch each other. It is also preferred that any non-oxidising or reducing flush gas is introduced from the opposite side of the pipe wall to the clad layer.

The inwardly tapered tubular end may have a large variety of shapes, and that the inward deflection may be determined by iterative calculation and/or experiments in order to asses that the amount of upset of the forge welded tubulars is reduced to a minimum.

The amount of material at the pipe ends deformed by forging is closely controlled to further minimise upset.

U.S. Pat. No. 4,669,650 discloses a forge welding process wherein the outer walls of the tubular ends are machined away to a greater depth that the inner walls of the tubular ends. The known configuration is, however, not configured such that the heated tubular ends are substantially cylindrical during forge welding operation.

Figure 12:
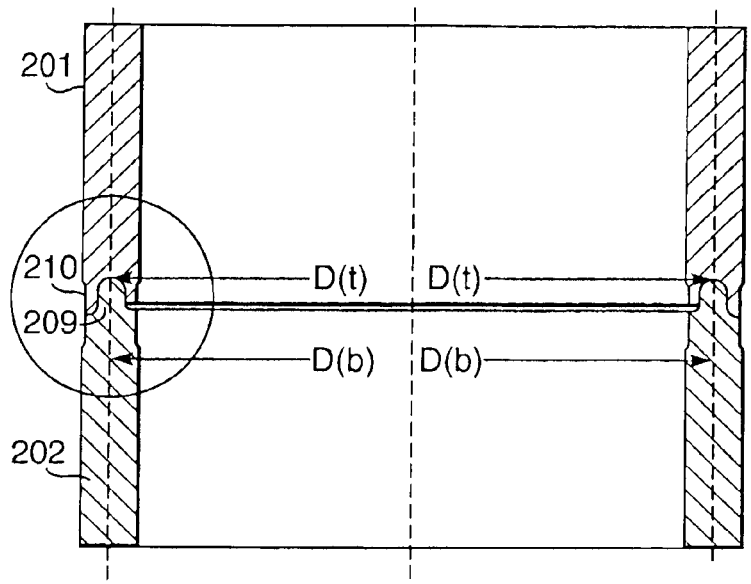
FIG. 12 shows a pair of concave and convex pipe ends that have been interconnected.
Figure 13:
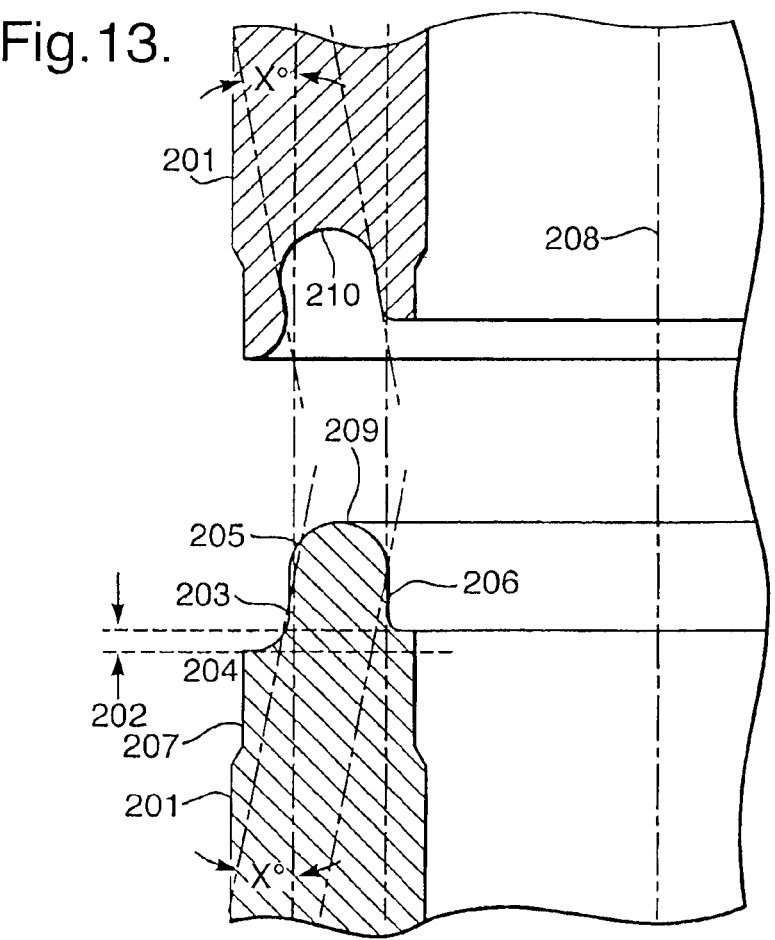
FIG. 13 shows how the concave and convex pipe ends are inwardly oriented at an inward sloping angle X which is selected such that the heated concave and convex pipe ends have a substantially longitudinal orientation.

In FIG. 12, a pair of heated axially aligned pipe ends is shown and in FIG. 13 the unheated ends are shown, wherein X is the inward sloping angle, 201=pipe having original wall thickness, 202=minimum forge length required to complete the weld, 203, 205, 206=typical radii of convex pipe end 209, 204=first contact shoulder, 207=pipe end having reduced wall thickness, 208=pipe center line and 210= concave pipe end. The sloping angles x of the unheated convex and concave pipe ends, 209, 210 illustrated in FIG. 12 are selected such that the heated pipe ends accurately intermesh and are accurately axially aligned as illustrated such that a seamless forge weld is created when the pipe ends 209 and 201 are pressed together and only minimal upsets are formed at the inner and outer surfaces of the pipes 201 in the region of the forge welded joint.

An outline of the dimensions of the pipe connection shown in FIGS. 12 and 13 is described in Table 1:

TABLE 1

Typical values for forge welding weld preparation - 4 mm WT, 70 mm OD pipe

| Identifier (see FIG. 1) | Description | Typical Value |
| --- | --- | --- |
| X | Inward sloping angle | 1 to 5°. |
| 1 | Original wall thickness | 4 mm |
| 3, 5, 6 | Preparation radii | 0.6 mm |
| 2 | Minimum forge length | 0.05 mm |
| 7 | Reduced wall thickness | 3 mm |
| 8 | Pipe centre line | |
| 4 | First contact shoulder | |

Table 1: Typical values for forge welding weld preparation —4 mm WT, 70 mm OD pipe.

Figure 14:
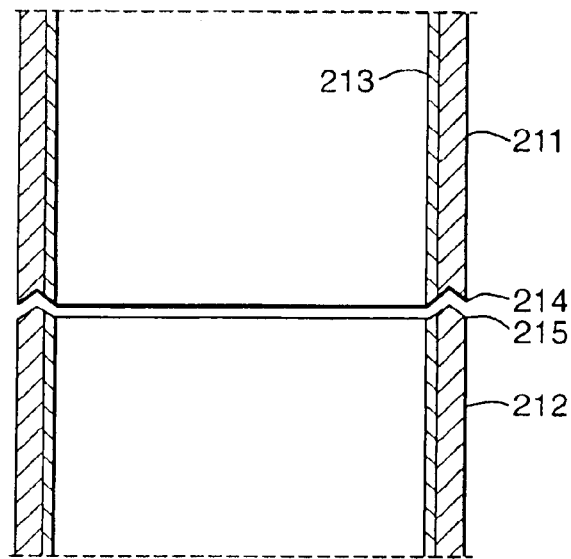
FIG. 14 is a longitudinal sectional view of a pair of cladded tubular ends just before they are joined by the forge welding method according to the invention.

Referring now to FIG. 14 there is shown an upper tubular 211 and a lower tubular 212 which each comprise a low grade steel base pipe have an inner cladding of high chromium steel 213.

The tubular ends 214 and 215 are wedge shaped such that the tips of the wedge shaped ends are formed by the claddings 213. This ensures that when the tubular ends are pressed against each other the claddings 213 touch each other before the ends of the base pipes touch each other.

Throughout the forge welding operation a flushing gas is flushed around the tubular ends 214 and 215 and to ensure continuation of the flushing between the tubular ends 214 and 215 after the claddings 213 touch each other, flushing gas is injected onto the uncladded outer surfaces of the tubulars 211 and 212.

Figure 15A:
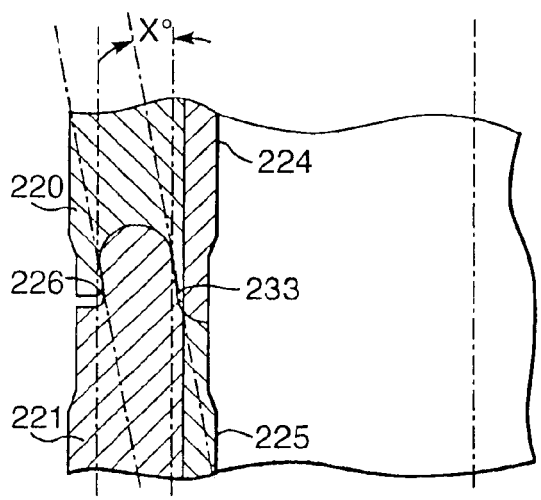
FIG. 15a is a longitudinal sectional view of a pair of internally cladded tubular ends wherein one tubular end is concave and the other tubular end is convex.

FIG. 15a depicts an embodiment where the lower end surface 226 of the upper tubular 220 has a generally concave shape and the upper end surface 223 of the lower tubular 221 has a generally convex shape.

The inner surface of the tubulars 220 and 221 may be cladded with a stainless steel lining 224 and 225 and the concave and convex end surfaces 223, 226 may be shaped such that the linings 224 and 225 touch each other first and that the base pipes 220, 221 touch each other thereafter and that the unheated end surfaces 223, 226 are inwardly oriented at a sloping angle X. In this case a reducing non-explosive flushing gas is injected from the exterior of the tubulars and the tubular ends still form a wedge such that the touching zone gradually increases from the outer surface towards the inner surface of the forge welded tubulars. In this way a good bond between the linings 224, 225 is produced and inclusion of oxides between the forge welded tubulars 220 and 221 is minimized.

Figure 15B:
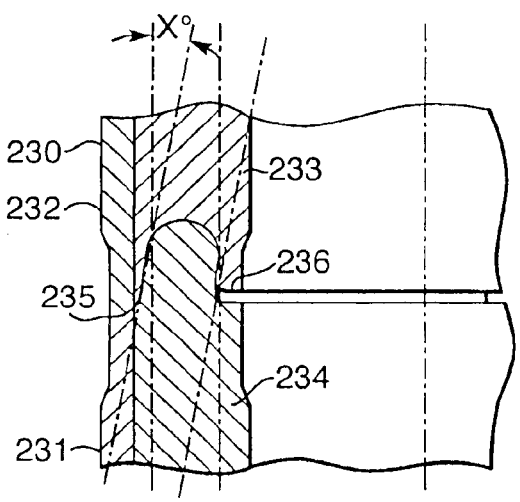
FIG. 15b is a longitudinal sectional view of a pair of externally cladded tubular ends wherein one end is convex and the other end is concave.

FIG. 15b illustrates a forge welded joint of a pair of low grade steel base pipes 233, 234 of which the outer surface is cladded with a stainless steel lining 230, 231 and of which the end surfaces 235, 236 have an intermeshing convex and concave shape such that the unheated end surfaces 235, 236 are inwardly oriented at a sloping angle X and that the stainless steel linings 230, 231 touch each other before the base pipes 233, 234 touch each other when the end surfaces 235, 236 are heated and pressed together during the forge welding operation. In this case a reducing gas is injected from the interior side 244 of the tubulars during the forge welding operation.

Figure 16:
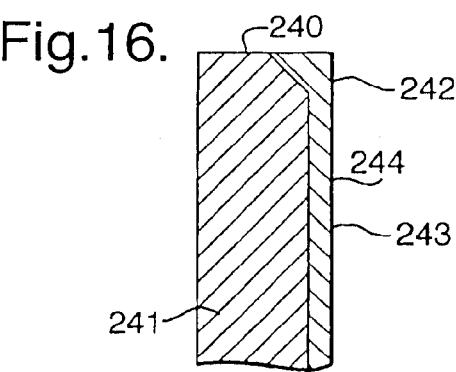
FIG. 16 is a longitudinal sectional view of an end of a cladded tubular wherein the thickness of the clad layer is increased at the end of the tubular.

FIG. 16 depicts a tapered wedge shaped end 240 of a pipe 241 that has been clad with a clad layer 243 and where further material 242 compatible with the clad layer 243 has been deposited around the end of the pipe 202 to allow further machining without exposing the base pipe 241. The inward sloping angle X of the tapered end 240 may be selected such that the heated pipe ends are substantially axially aligned and the taper angle is selected such that the clad layers 243 of adjacent pipe ends touch each other first before the base pipes touch each other during a forge welding operation.

In another embodiment of the present invention, the invention includes an improved method for forge welding of heavy duty tubulars such that a welded connection of high strength and quality is obtained.

Heavy duty tubulars may be formed by oilfield, well and/or other tubulars which are in use subject to high mechanical and/or thermal stresses as a result of their use in an irregular borehole or hostile on- or offshore environment. Thus the heavy duty tubulars may frequently be subject to large radial, tangential and/or shear stresses which cause a high elastic, plastic and/or pseudo plastic deformation of the tubular wall and any tubular joints. The heavy duty tubulars may be tubulars which are expanded downhole to a larger diameter and plastically deformed during the expansion process, drill pipes which may be 10 kilometers long and twisted over 30 times of the pipe circumference as a result of the torque transmitted to the drill bit and friction between the drill pipe and the irregular borehole wall or heater well casings, steam injection and/or other heater pipes which are subject to high thermal expansion and may be squeezed by the thermal expansion of the surrounding formation and/or subsidence during the production operations.

In accordance with this embodiment of the present invention there is provided an improved method of joining heavy duty tubulars, the method comprising joining the tubulars by forge welding and flushing a reducing flushing gas around the heated tubular ends during at least part of the forge welding operation such that oxides are removed from the forge welded tubular ends and the amount of oxide inclusions and irregularities between the forge welded tubular ends is limited, wherein the tubular ends have a non-planar shape.

The tubular ends may have in circumferential direction a complementary teethed sinusoidal shape in order to alleviate forces to the forge welded tubular ends during use of the heavy-duty tubular string. The intermeshing teethed or sinusoidal ends may be pressed against each other during the forge welding operation by moving the tubular ends in a longitudinal direction towards each other during the welding process, whilst the circumferential orientation of the tubular ends is controlled such that along the entire circumference a gap of a substantially constant width is present during the heat up phase.

The non-planar shaped tubular ends preferably have a regular intermeshing sinusoidal or teethed shape in order to inhibit in particular shear stresses on the forge welded joint when the tubular string is twisted and/or radially expanded while the tubular string is rotated and/or radially stretched in a cavity, such as an underground borehole.

In such case the tubular ends may be heated by passing a high frequency current in circumferential direction through the tubular walls near the tubular ends that are to be joined and wherein the presence of cold spots along the circumference of the heated tubular ends is reduced by arranging a series of longitudinal ferrite bars around the outer surface of the tubular ends and/or within the interior thereof. Furthermore the tubular ends may be heated by passing high frequency electrical current through the tubular ends by means of a series of electrodes which are pressed against the inner and/of outer surface of the tubular end adjacent to the tips of the teeth and/or sinusoidal end faces.

The heavy duty tubular string may be a casing while drilling string, which carries a drill bit while drilling the hole and which remains in the borehole in an expanded or unexpanded configuration after completion of the drilling process.

The tubulars may also be joined downhole by forge welding after a tube expansion operation wherein a spear is inserted into the region of the tubular ends which then heats the tubular end to a forge welding temperature and presses them together the spear flushes a reducing flushing gas around the heated tubular ends during at least part of the forge welding operation.

In such case the ends of the tubulars may at least partly overlap each other and the spear and or other forge welding device is inserted into the inner tubular which heats up the tubular end, flushes a reducing flushing gas into any gap remaining between the overlapping tubular ends and which subsequently presses the outer surface of the heated end of the inner tubular against the inner surface of the outer tubular to join said tubular ends by forge welding.

In such case the partially overlapping tubular ends are teethed or have a complementary sinusoidal shape in order to alleviate the presence of abrupt stress variations to the forge welded expanded tubular ends when the tubular string is bent, compressed and/or otherwise deformed.

Figure 17:
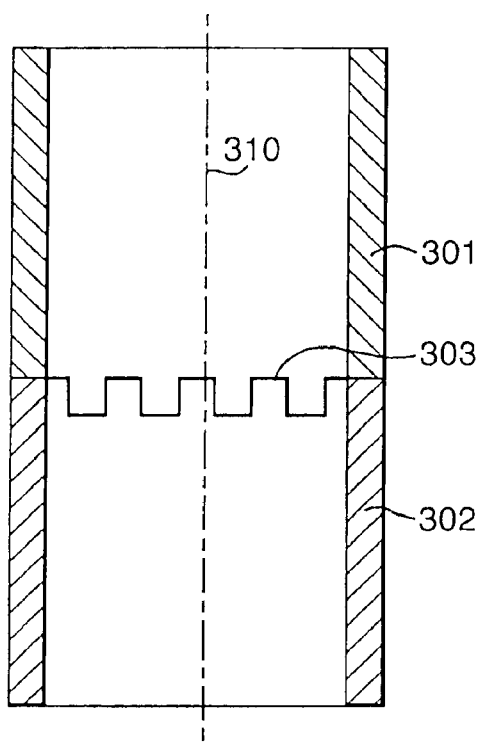
FIG. 17 shows two pipe ends with complementary teethed end faces. The teethed end faces can be used to align the tubulars in angular direction.

As illustrated in FIG. 17 welding of the teethed ends 303 of adjacent pipes 301, 302 together along the length of the contour of the intermeshing non-planar teethed ends 303 which are rotation symmetrical relative to a longitudional axis 310 of the pipes 301, 302 provides a total length of the weld which is larger than the total circumferential length of the pipes and thereby reduces the loading of the weld compared to that of the pipe body.

Figure 18:
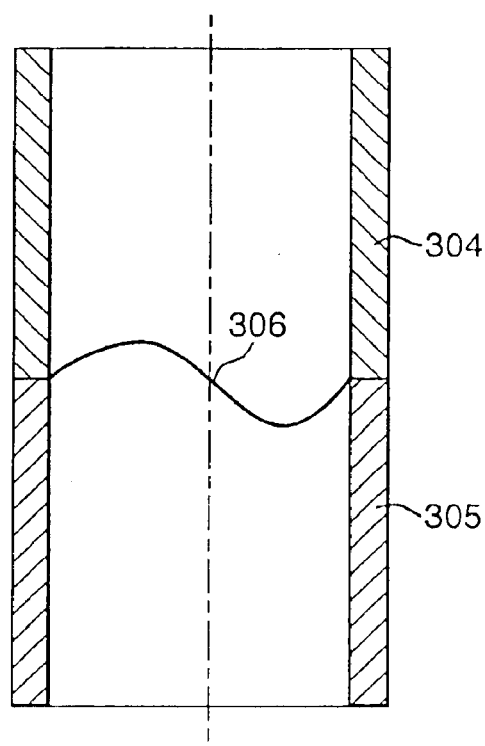
FIG. 18 show two pipe ends with complementary non-planar end-faces, which are in this case of a sinusoidal shape.

In FIG. 18 the non-planar ends 306 of two adjacent pipe sections 304 and 305 have an-in circumferential direction sinusoidal shape, which is rotation symmetrical relative to a longitudinal axis 311 of the pipe sections 304 and 305.

Figure 19:
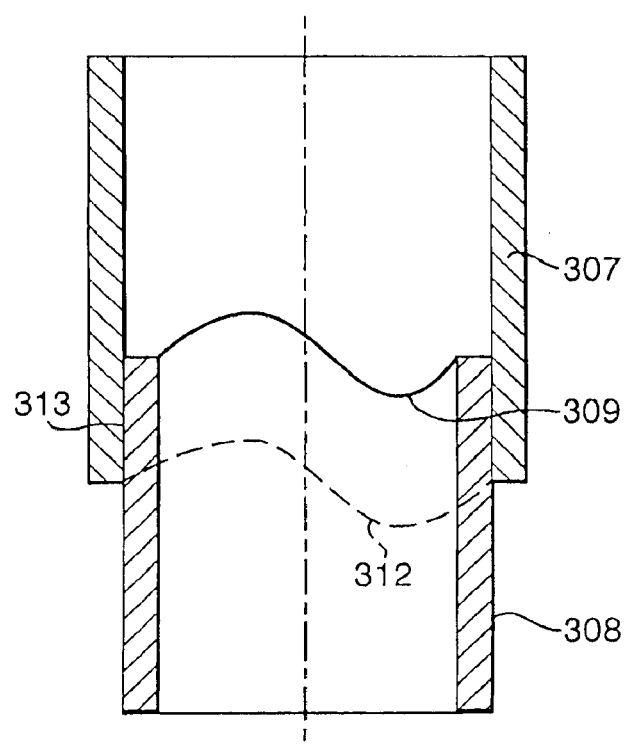
FIG. 19 shows two partially overlapping pipe ends of which the end surfaces have a sinusoidal shape.

FIG. 19 shows two pipe ends 307 and 308 that are partly overlapping. The inner pipe end 308 is provided with a non-planar rotation symmetrical sinusoidal end face 309 in contact with the outer pipe 307, whereas the outer pipe 307 has a non-planar rotation symmetrical sinusoidal end face 312 in contact with the inner pipe 308. Welding of the pipes 307 and 308 together along the length of the overlapping pipe sections 313 between the non-planar end faces 309 and 312 yields a weld length that is larger than the length of the circumference of the pipes and thereby reduces the loading of the weld compared to that of the pipe bodies. In addition, this configuration yields a gradual transfer of the loading from one pipe body to the other pipe body and supports the mitigation of stress concentrations in the overlap zone of the pipes when the pipes are twisted by torsional forces and/or bent and/or radially expanded.

In accordance with an embodiment of the invention the tubular ends are heated to a predetermined temperature above 1200 degrees Celsius and surrounded by a hydrogen containing shield gas when the tubular ends are pressed together, whereupon the forge welded tubular ends are cooled down rapidly from said temperature above 1200 to at most 600 degrees Celsius within 3 minutes after the forge welding operation.

Optionally, the forge welded tubulars comprise a high carbon steel grade and are cooled down from above 1200 to at most 600 degrees Celsius within one minute after the forge welding operation.

The forge welded tubulars may be cooled by flushing the tubular ends with cold liquid nitrogen, helium, argon or liquid carbon dioxide.

The forge welding method may be used to join a large variety of steels and alloys including stainless steels and pipeline steels. The method according to the invention is particularly suitable for joining oil country tubular goods (OCTGs) for which controlled cooling and/or post weld heat treatment is often required to be done at remote locations. OCTGs are generally made of a group of steels that are sutiable for use as dwnhole well casings and production tubings in the oil industry and are specified by international standard ISO 11960 and American standard API 5CT. With the exceptions of two grades, which contain significant quantities of chromium, these materials are carbon steels.

Historically OCTG materials have been joined using threaded couplings and this has avoided any requirement for them to be welded. As a consequence high strength OCTG materials contain relatively high levels of carbon and manganese and are considered "unweldable" using traditional fusion welding technology. However the materials can be welded using forge-welding techniques such as shielded active gas, friction welding and flash butt welding, because these are solid-state processes in which joining occurs at relatively low temperatures.

Unfortunately the metallurgy of high carbon steel grades requires that special steps are often necessary to allow the best combination of properties to develop after forge welding, particularly with respect to impact properties. In general a controlled rapid cool down of the welded tubular ends will minimize the heat affected zone and will ensure that acceptable properties are achieved following forge welding.

In addition a particular requirement has been identified for those welding techniques that take place in dry reducing gas or gas mixtures (eg. shielded active gas forge welding) to ensure that the welding area is kept free of water and heavy hydrocarbons. This limits the use of traditional water and oil based cooling quenching fluids in the particular application and requires alternative quenching media.

When high carbon steels are cooled from the fully austenitic state (eg. the welding temperature) in air they are inclined to adopt a structure consisting of martensite with a small amount of relatively brittle bainite. This can lead to acceptable bend and strength characteristics but low impact resistance. To avoid formation of any relatively brittle phases it is necessary to rapidly cool the steel from a fully austenitic structure (typically 900–700° Celsius depending on the steel being used) to approximately 300° Celsius within a short time, typically 1 minute.

During manufacture of OCTGs containing high levels of carbon it is standard practice to improve mechanical properties by heating into the fully austenitic region and quenching into a forced circulating water bath to obtain a fully martensitic structure. This treatment is followed by heating at approximately 600° Celsius for a predetermined amount of time, often several hours, to produce a tempered martensitic structure with appropriate, acceptable mechanical properties. This process is called quenching and tempering (Q&T).

In an embodiment of the present invention, the problem is solved of the heat treatment requirements and equipment for producing forge welds in high strength high carbon OCTG steels with acceptable impact properties. Several embodiments of an internal spear that is inserted into the interior of the tubulars in the welding zone may be used to control the cool down process of the forge welded tubular ends depending on the steel grades of the tubulars and the particular circumstance of the weld.

In addition the internal spear may be utilized for a variety of other functions, such as alignment of the tubulars, sealing off the interior of the tubulars in the welding zone and control of the quality of the forge weld by an electromagnetic acoustic transmission (EMAT) or other automated weld inspection technique.

Water, water based, oil and oil based quench media may be used with forge welding techniques such as flash butt welding and various means of friction welding which do not require a dry welding environment. In specific applications, such as on a rig, conventional oil field fluids such as mud and brine may also be used as quenching media.

With processes where a dry environment is needed these media may also be used provided quenching is carried out internally. However with a wall thickness in excess of approximately 5 mm, when external quenching is also required, they are not ideal because they may slow down the welding process while the area is allowed to dry or require a second station to avoid contamination of the weld station or require a self contained quenching facility to prevent contamination of the welding area and this may be complex to construct. In order to avoid these drawbacks alternative safe quench media may be used. These include helium, nitrogen, argon and other non-flammable, volatile mixtures that will evaporate quickly following use or various combinations of these.

Figure 20:
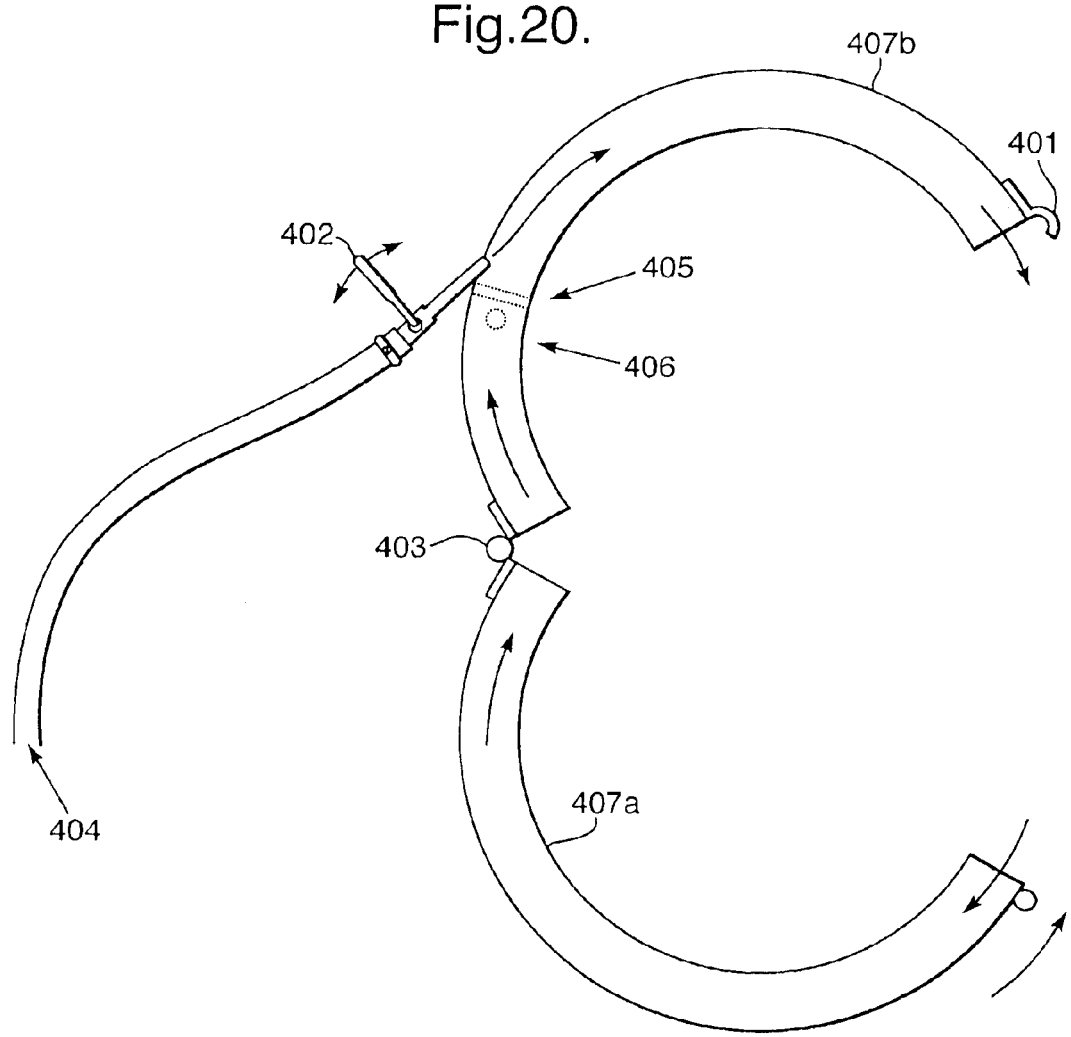
FIG. 20 is a schematic cross-sectional view of an external shield gas chamber in which a cold fluid is injected during the cool down phase after a forge welding operation.

In its simplest variant, in-situ quenching of welds can take place externally using a portable collar 407A, 407B as indicated in FIG. 20 using quench media, such as liquid nitrogen, argon, carbon dioxide or an aqueous liquid. The collar 407A, 407B shown in FIG. 20 is manufactured with a hinged fastening 403 and an inside diameter to match a particular pipe outer diameter (OD). The collar 407A, 407B thus forms a split ring which, when closed, will fully encircle the welded area of pipe and fasten around it using the fastener 401. In operation the welded area is fully encircled with the split ring that is fastened with 401, a supply of quench media is available through the supply hose 404 and is released into the interior of the split ring collar 407A, 407B by opening the valve 402. Quench media circulates through the split ring collar 407A, 407B until it reaches the baffle 405 whereupon it exits via a drain hole 406.

This split ring collar 407A, 407B is applied and quenching started, as soon as possible after welding and, in any event, before the weld area can cool below the austenising temperature of the steel being joined (typically 900 to 700° Celsius depending on carbon content).

The split ring collar 407A, 407B may be integrated into a gas shielding chamber or hood into which a reducing shield gas comprising about 95 vol % nitrogen and about 5 vol % hydrogen may be injected during the forge welding operation or integrated with the heating mechanism with little modification.

Figure 21:
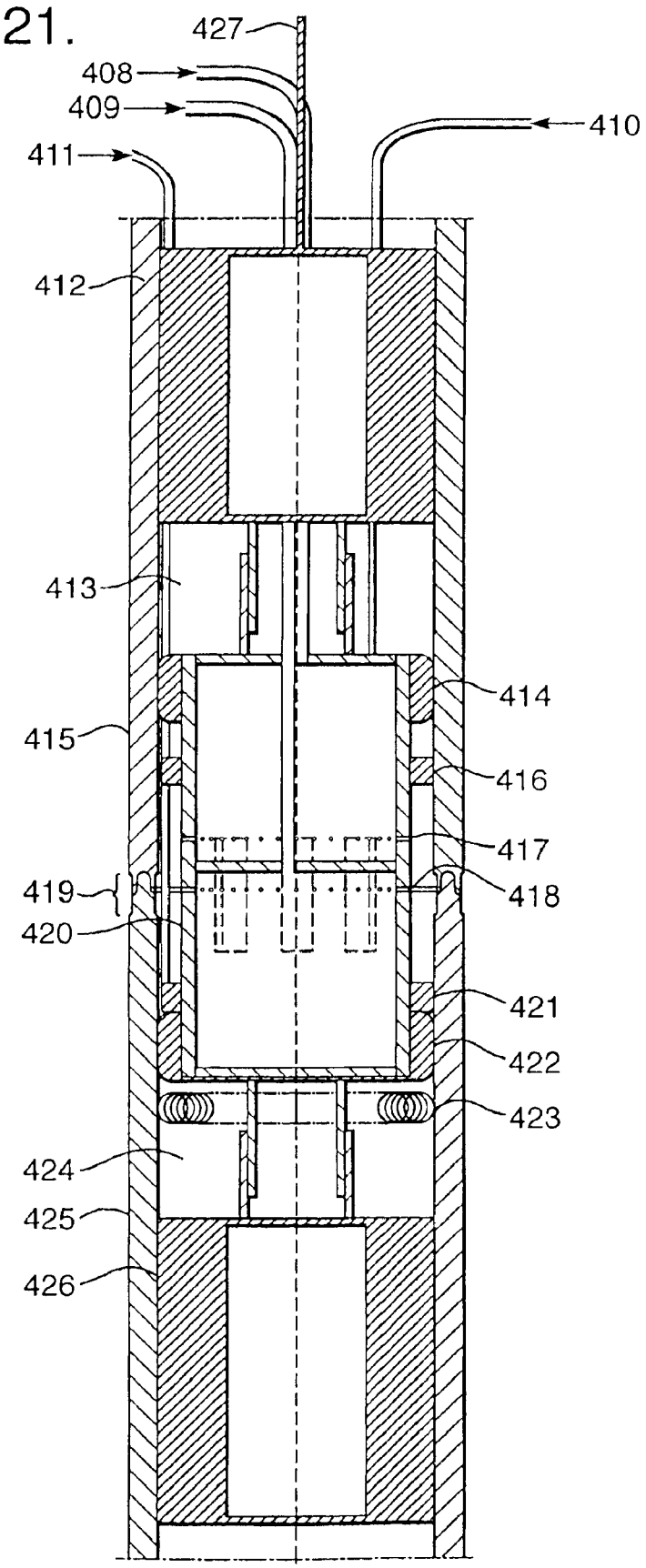
FIG. 21 is a longitudinal sectional view of an internal spear via which a cooling fluid is injected towards the forge welded tubular ends after the forge welding operation.

For thicker wall tubes, where the cooling rate may vary significantly through the wall, external quenching may need tube used in conjunction with internal quenching using an internal spear 430 as illustrated in FIG. 21. This is principally dependant on the metallurgy of the steel in question, particularly carbon content, and the quench media employed. For standard OCTG materials through-wall cooling to approximately 300° C. is preferably be done in approximately 1 minute.

For certain applications, such as thin wall tube and low carbon steel it is possible to quench the steel from a fully austenitic structure to fully martensitic using an internal spear 30 as shown in FIG. 21 as an alternative to external quenching as shown in FIG. 20. Further, for thicker steel sections and higher carbons steels it is necessary to use a combination of internal and external quenching to ensure even and rapid cooling across the pipe wall.

The spear 430 is inserted into the interior of an upper pipe 415 and a lower pipe 425 in the region of the forge welded pipe ends 419.

The spear 430 may comprise a number of elements which may be used conjointly or in isolation. The major elements of the spear 430 shown in FIG. 21 are a support cable string 427 for deployment and retrieval and data and power lines, shield and/or cooling fluid supply and discharge hoses 408, 409 hydraulic fluid supply and discharge hoses 410, 411, expandable gripping elements 412, 426, compression elements 413, 424 to draw the upper and lower sections of the spear 430 together and provide axial forge force, EMAT inspection probe assemblies 414, 422, inflatable gas sealing elements 416, 422 to allow isolation of weld area 419 to flush with a non-oxidising and/or reducing shield gas, outlet nozzles 417 for flushing gas and/or cooling fluid from inside of pipe and return nozzles 418 for shield gas and/or cooling fluid. The internal spear 430 incorporates ferrite bars 420 to provide additional control for high frequency current and induction heating, and an induction coil 423 for provision of heat for forge and/or post weld heat treatment.

It should be noted that not all of these elements may need to appear in every spear 430 but that any combination of the elements described above is possible. In addition, alternative-heating elements incorporating pairs of contacts positioned above and below the weld area 419 for heating using eg. resistance are also options.

With some forms of forge welding the internal spear will require additional detailing to facilitate objectives such as provision of flushing gas, alignment, pressure isolation, to influence heating etc in addition to the requirement to supply quench media. These are described in more detail below.

The internal spear 430 may be used horizontally, for pipelines/pipework, or vertically inside a well casing and tubing. It may be positioned in the upper pipe 415 before the pipe 415 is moved on top of the lower pipe 425 into position for welding or inserted into the interior of the aligned pipes 415, 425 immediately prior to welding.

The spear 430 is suspended from a supporting cable string 427, for insertion and retrieval. The spear 430 runs through the upper pipe 415 to be welded. One end of the fluid supply and discharge hoses 408, 409 terminates outside of the upper pipe 415 at a station that provides cooling and/or shield gas media through a pump; the other end is fastened inside a cylindrical housing of the spear 430 which, for some forms of forge welding, such as shielded active gas and flash butt welding, is required to be non-metallic. The spear 430 is sized to drift through the pipes 415, 425 being joined. The spear 430 has preferably about equally spaced cooling-nozzles 418 embedded around the tubular's central portion in which the ferrite bars 420 are embedded. The number and size of nozzles 418 is dependent on the size of the housing, which is determined by the internal diameter ID of the pipes 415, 425 being joined, the cooling media and pump capacity.

The gripping elements 412, 426 on both sides of the spear 430 ensure that it remains approximately equidistant from the pipe walls.

Immediately after the forge weld has been made, quench media is pumped through the supply hose 408 and out through the nozzles 418 to cool the welding zone 419 rapidly. If necessary this is done simultaneously with external quenching by means of the split collar 407A, 407B shown in FIG. 20.

The spear 430 may fulfill several functions when used in conjunction with a number of forge welding processes, such as provision of flushing gas to improve weld quality and optional low pressure sealing ability to isolate the weld area and subsequent provision of quenching media to improve mechanical properties The flushing gas may be a non-oxidising or non-explosive reducing gas comprising about 95 vol % Nitrogen and about 5 vol % hydrogen Non-oxidizing gases may be required when using flash butt welding, induction heated forge welding, friction welding or a combination of these methods such as thermo-kinetic welding for example. A reducing gas or gas mixture may be required when using shielded active gas forge welding or induction heated forge welding for example.

The ferrite bars 420 serve to improve the heating effect of induction and resistance/induction heating The split external cooling collar 407A, 407B shown in FIG. 20 and the internal spear 430 shown in FIG. 21 are appropriate to a range of welding processes such as friction welding, flash butt welding, shielded active gas welding etc. whenever post weld heat treatment is required. Heating for tempering purposes may be carried out from inside the pipe, from outside the pipe or in combination. Combined heating may be particularly effective in the case of thick wall pipe (pipe wall thickness approximately >5 mm).

Whenever tempering is carried out in a hazardous area it is, necessary to ensure compliance with safety conditions. This may be accomplished using a variety of well-known techniques such as provision of a non-flammable blanket gas and a double walled hermetically sealed explosion resistant shield gas chamber.

The internal spear 430 shown in FIG. 21 may have an integral induction-heating coil 423 that is centered over the weld area and powered through an umbilical cable. Where the spear 430 includes components such as injection nozzles 418 and/or ferrite bars 420 then the induction coil 423 may be installed in a secondary housing and moved into position over the weld area immediately prior to use. The relatively through-wall nature of induction heating allows tempering of a fully martensitic structure in a comparably short time, usually no longer than 4 minutes depending on the precise metallurgy of the welded area.

An additional external heating coil (not shown), which is well documented technology, may be centered over the weld area 419 using spacers as indicated, and powered to allow tempering. The external heating coil may consist of a split ring embedded in the split collar 407A, 407B shown in FIG. 20 or may consist of a fully encircling coil. Where the proximity of the coil to metallic fixtures around the weld station are likely to cause extraneous heating then the coil is positioned some short distance form the weld station. When welding is done in a sealed chamber formed by the collar 407A, 407B containing shield gases, whether they are non-oxidizing or reducing, then it is preferred to position the coil inside this chamber.

The relatively through-wall nature of induction heating allows tempering of a fully martensitic structure in a comparably short time, usually no longer than 4 minutes depending on the precise metallurgy of the welded area.

For thick wall pipes 415, 425 it may be preferable to heat using a combination of internal and external coils in an internal spear 430 and external collar 407A, 407B to ensure even heating across the pipe wall. In this variation both coils are powered independently and simultaneously.

The internal spear 430 shown in FIG. 21 may have resistance heating contacts (not shown) located circumferentially around its periphery equidistant above and below the welding zone 419. Current, typically 400 Amps, is passed between these contacts through an umbilical cable to heat through electrical resistance. Heating is controlled by an optical or contact pyrometer located inside or outside the pipe that is in a control loop which regulates the passage of current.

Where the spear 430 includes components, such as injection nozzles 418 and/or ferrite bars 420, then the resistance contacts will be installed in a secondary housing attached to the primary housing and moved into position over the weld area 419 immediately prior to use. The relatively through-wall nature of resistance heating allows tempering of a fully martensitic structure in a comparably short time, usually no longer than 4 minutes depending on the precise metallurgy of the welded area 419.

Optionally, external electrical contacts may be positioned above and below the welding zone 419 in the configuration described in FIG. 21. Where the proximity of the external contacts to metallic fixtures around the weld station are likely to cause extraneous heating then the contacts may be positioned some short distance from the weld station and moved into position as and when required. When welding is done in a sealed chamber containing shield gases, whether they are non-oxidising or reducing, then it is preferred to position the contacts inside this chamber.

The relatively through-wall nature of resistance heating allows tempering of a fully martensitic structure in a comparably short time, usually no longer than 4 minutes depending on the precise metallurgy of the welded area.

For thick wall pipes 415, 425 it may be preferable to heat the pipe ends 419 using a combination of internal and external contacts to ensure even heating across the pipe wall. In this variation both sets of contacts are powered independently and simultaneously.

Certain applications of welded tubulars require non-destructive testing of the weld prior to use. In these applications inspection probes 414, 422, such as conventional ultrasonic, EMAT or other probes may be incorporated into the internal spear 430 as appropriate.

It may be beneficial for certain materials being welded using forge welding to be heat treated prior to use to improve their mechanical or corrosion properties. In these instances a heating device such as the heating coil 423 shown in FIG. 21 may be incorporated into the spear housing or added as an accessory in an additional housing. Particularly with smaller diameter pipes 415, 425 this heating device may be used as the primary heating device for forge welding.

In certain circumstances, especially with larger diameter tubulars, gripping and compression devices 412, 414, 422, 426 may also be incorporated into the internal spear 430. This has the advantage that an additional external device, such as the split collar 407A, 407B shown in FIG. 20, is not required, so that the spear 430 can be employed to forge weld tubulars downhole in a well.

An embodiment of the invention comprises radially expanding tubulars that have been joined by forge welding whilst flushing a reducing flushing gas around the heated tubular ends during at least part of the forge welding operation such that oxides are removed from the region of the forge welded tubular ends and the amount of irregularities between the forge welded tubular ends is limited.

The tubulars may comprise slots and/or other perforations at or near the forge welded ends, which slots and/or other perforations are filled with a heat resistant filler during the forge welding process.

Optionally, the tubular ends are heated by passing a high frequency current in circumferential direction through the tubular walls near the tubular ends that are to be joined, and the heat resistant filler comprises an electrically conductive ceramic material. In addition, where it is desirable to provide a gas seal around the weld area to allow flushing with non-oxidising or reducing gas or gas mixtures extended internal and external sealing regions are required.

The tubular ends that are to be joined may both be expanded and folded into a substantially similar dented or corrugated shape before the forge welding operation, whereupon the dented or corrugated tubular ends are forge welded together and are unfolded into a substantially cylindrical shape during the subsequent tube expansion process. In such case the tubulars may have an un-slotted, substantially continuous, wall in the region of the welded ends and comprise an array of staggered slots and/or other perforations away of the welded ends, such that when the tube is expanded the welded initially dented or corrugated tubular ends unfold to a substantially cylindrical shape and the slots and/or other perforations are widened Expandable slotted tubulars as shown, for example, in FIGS. 22–26 may be used in oil and gas wells to control e.g. sand production. For this purpose the tubulars may wrapped with an assembly of screens with a specific mesh size to prevent sand from entering into the hole during production. The tubulars with the screens wrapped around them are supplied to the well location in lengths of typically 10 m. It is known from U.S. Pat. No. 5,924,745 to connect the overlapping ends of expandable tubular sections by slotted thread connections.

The slots in both parts of the thread connections are aligned and locked during make-up of the tubular on the rig. Once the tubular has reached its target depth in the hole it is expanded by pushing a cone through the tubular to ensure an intimate contact between the outer wall of the expanded tubular and the formation or casing inner wall.

The slotted connections known from U.S. Pat. No. 5,924,745 are designed in such a way that the expansion force required at the cone to expand the connection is similar to that of the slotted pipe itself. This is essential because it enables the cone to be pushed down the hole without the risk of buckling the un-expanded pipe section below the cone.

However, the known slotted connections are expensive elements of the tubular and the make-up of the connections while running the tubular into the hole is a critical operation.

The forge welding method according to the invention aims at replacing of the threaded connection known from U.S. Pat. No. 5,924,745 by a welded, connection to overcome the disadvantages of the threaded connections.

Figure 22:
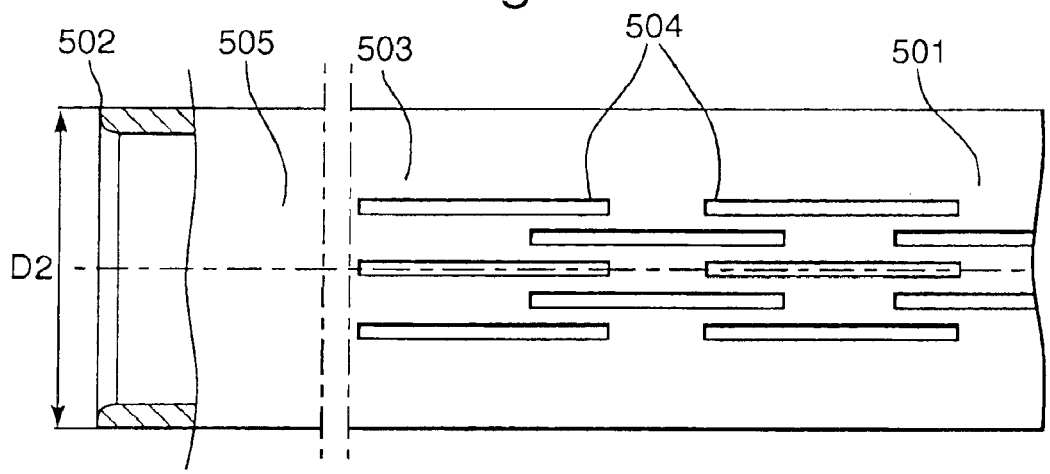
FIG. 22 depicts a partially longitudinal sectional and partially side view of a slotted tubular at the diameter after installation.

The method according to invention may be used to forge weld the ends of a partially slotted tubular 501 as shown in FIG. 22 to the ends of adjacent partially slotted expandable tubulars (not shown).

The unexpanding tubular 501 has a diameter D2 which is at least 10% smaller to than the diameter of the expanded tubular (not shown) after expansion in the hole. The end faces 502 of the tubular are machined as per the requirements for the welding process to be applied on the rig site. The middle section of the tubular 503 is provided with slots 504 leaving solid sections 505 of pipe at both ends of the tubular.

Figure 23:
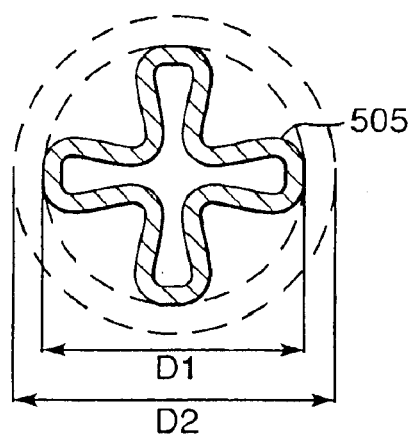
FIG. 23 depicts a cross-sectional view of the tubular of FIG. 22 after the tubular end is folded into a corrugated shape.

FIG. 23 shows the solid, unslotted, end section 505 which is folded in such a way that the outer diameter of the section equals the diameter D1 of the unexpanded tubular while running into the hole.

Figure 24:
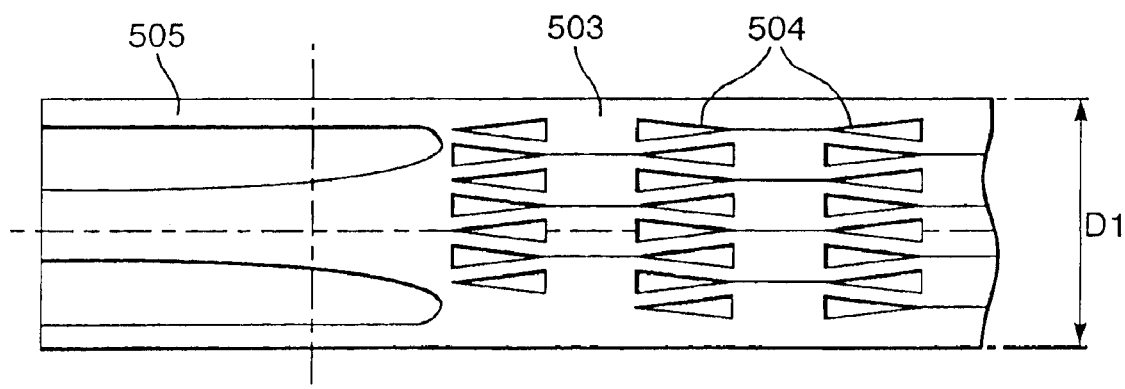
FIG. 24 is a side view of the tubular shown in FIG. 23 showing the transition from the slotted mid section towards the corrugated end, which is subsequently forge welded to a corrugated end of an adjacent tubular.

After that the middle section 503 is also reduced to the same diameter D1 by compressing the slots machined in the pipe body which is shown in FIG. 24. This implies that the middle section remains cylindrical. Finally the tubular 24 is provided with an expandable sand-screen assembly (not shown).

On the rig the corrugated end sections 505 of two tubular sections are welded together by forge welding whilst a reducing flushing gas is flushed around the heated tubular ends during at least part of the forge welding operation. Once the string of unexpanded tubulars joined by forge welding has reached the target depth a cone is pushed through the tubular string from top to bottom or vice versa. The slotted pipe body is thereby expanded to an enlarged diameter D2 and the corrugated end sections of the joints which are forge welded together are unfolded and reach their original diameter again, which is similar to the diameter D2 of the expanded slotted tubular sections.

Advantages of the forge welded connection are:

Handling of the tubular joints on the rig site is drastically simplified because alignment of the tubular joints is easily done by aligning the corrugated end sections of the joints.

The end sections of the joints are not slotted which facilitates the heating process; there is a continuous path for the current flow.

The cone force required to shape-the solid end sections of the slotted-tubulars is much lower than the force required to expand the section because the end sections are only "unfolded"; no increase of the circumferential length of the tubular is required.

A large diameter ratio between the tubular while running into the hole and after installation because this ratio is not limited by the maximum expansion ratio of solid tubulars.

The diameter ratio is governed by the percentage of the circumference of the tubular that is provided with slots.

An alternative process and embodiment of the welded slotted tubular comprises a tubular with an initial diameter equal to that required for running the tubular into the hole. Both end sections of this solid tubular are expanded to the diameter of the tubular after installation in the well. The middle section and part of both expanded end sections are provided with slots. Then the expanded end sections (solid and slotted part) are folded to reduce their diameter again to that of the slotted part of the tubular.

After this, the procedure is identical to that described above. The limitation of this process is that the maximum diameter ratio between pre and post expansion that can be achieved is governed by the maximum expansion ratio of the solid pipe.

To prevent the slots or perforations which are a necessary element in a variety of expandable tubulars welding together during the forge weld process it is necessary to fill the slots or perforations with a non-weld-able material which will not interfere with the welding and expansion processes.

Figure 25:
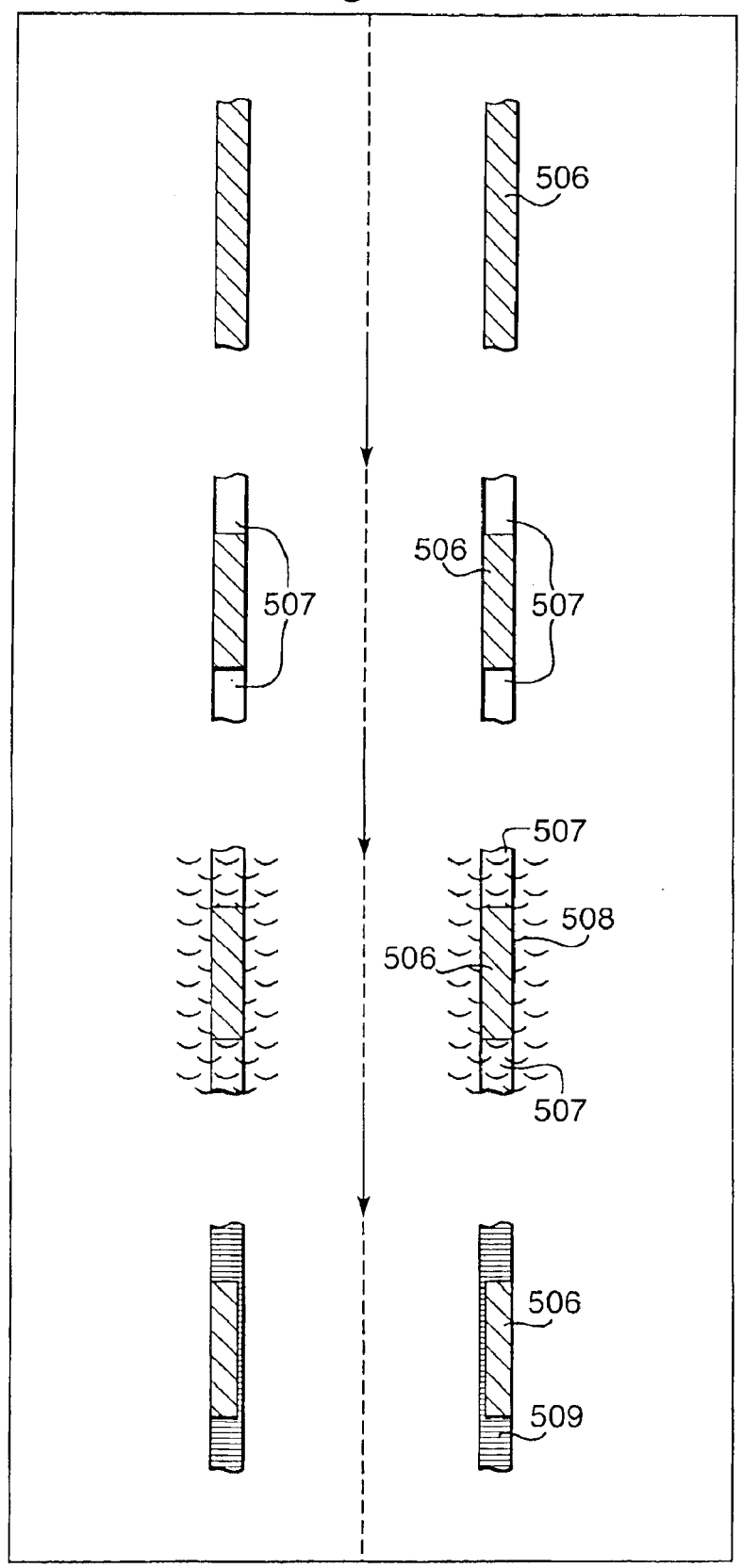
FIG. 25 is an illustration of the steps required in an embodiment of a technique to ensure that the slots or perforations created in various expandable tubulars are filled with a refractory material to allow the pipe ends to be forge welded without the slots or perforations being welded together.

FIG. 25 illustrates the steps required to fill the slots or perforations with ceramic slurry that sets inside the slots or perforation. The first step in the operation, indicates a solid tubular 506 prepared for slotting or perforating. Slots or perforations 507 are then cut. In some variations of the technology slots and/or perforations are cut in a flat sheet which is then worked into tubulars. Both of these alternative methods may be used to produce slotted/perforated expandable tubulars. For forge welding it is sometimes advantageous to increase the width of slots which intersect the free surface of the tube butt end for a distance of approximately 1–2 mm from the butt end. Once the slots or perforations 507 are made a coffer (not shown) is positioned around the ends of the tubulars and the area is flooded with ceramic slurry 508. Vibration may be applied to ensure that the slurry completely fills the perforations or slots 507. It is necessary for the coffer to encompass an area of the tubular 506 extending from above the tip of the tubular to a region covering at least two rows of perforations or slots. Typically this would require a depth of coverage of approximately 100 mm. Finally, excess ceramic is removed, leaving the slots or perforations 507 completely filled with ceramic filler 509.

During welding of the butted pipe ends it is often advantageous to flush the weld area with a reducing or non-oxidising gas or gas mixture. To accomplish this with slotted or perforated expandable tubulars it is necessary to ensure that the area containing the slots is completely sealed.

Figure 26:
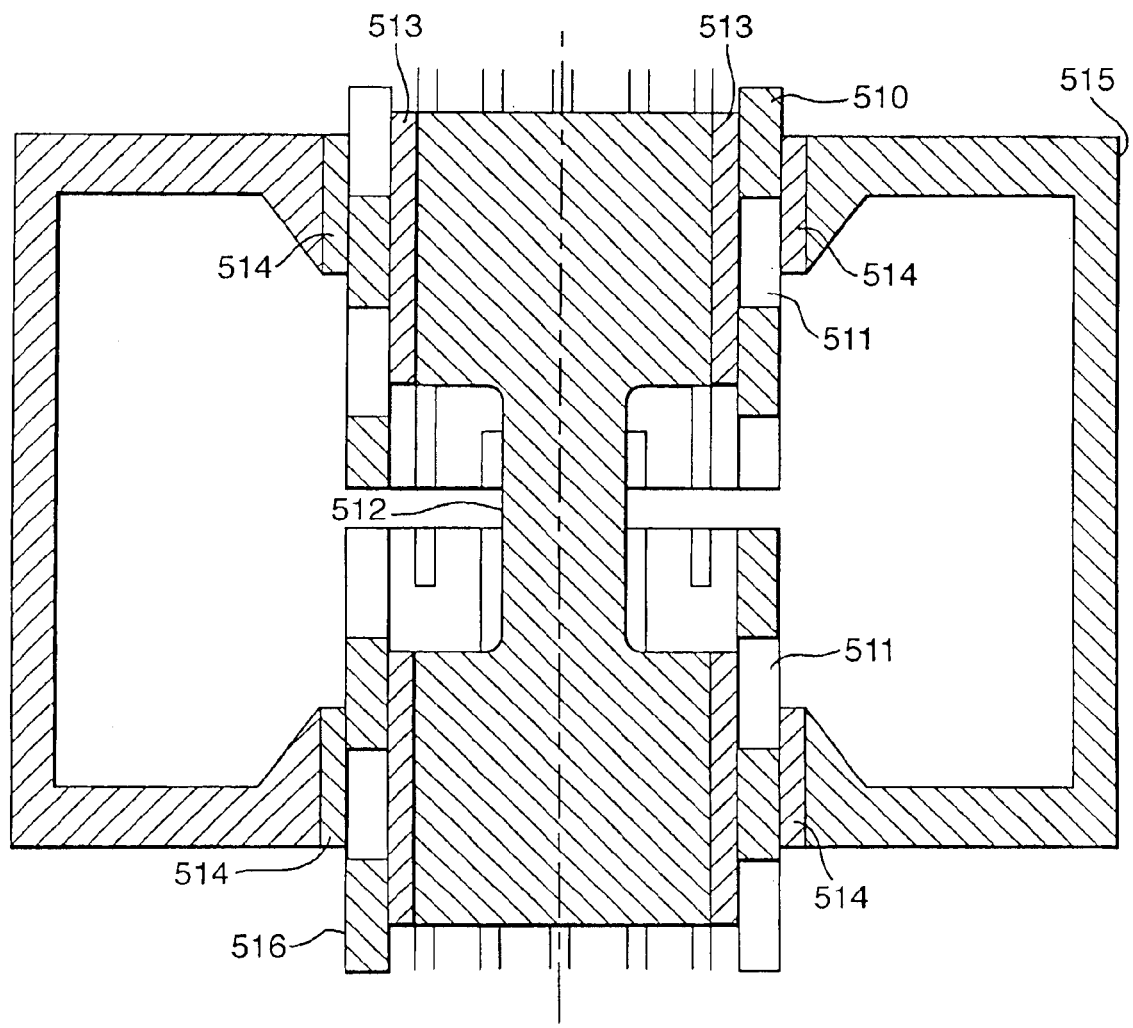
FIG. 26 depicts a seal assembly for forge welding of a slotted or perforated expandable tubular in which internal and external sealing areas have been significantly extended beyond that used for non-slotted and non-perforated tubulars.

FIG. 26 illustrates a simple method to accomplish this. A sealing device 512 is positioned inside the upper and lower pipes 510, 516. The sealing device 512 comprises sealing elements 513 that are of a sufficient length to completely cover at least two rows of slots or perforations 511. This configuration ensures that the internal area at the ends of the pipes 510, 516 is sealed to allow gas flushing. In addition to the internal seal an external sealing chamber is also required. This sealing chamber has extended sealing elements 514, which are designed to completely cover at least two rows of slots or perforations 511.

The requirement to completely cover at least two rows of slots or perforations 511 as described above is the preferred embodiment however where the slots or perforations do not overlap it is acceptable to cover only a single row, although this increases the risk of leakage. In an embodiment of the present invention, the invention includes creating a cavity into an end surface of one of the tubular ends that are to be joined, inserting a marker into said cavity and subsequently joining the tubular ends.

The tubular ends may be joined by welding, such as forge welding, or may be pressed together by a screw thread connector.

The thus inserted marker may comprise an electronic tag such as a passive radio frequency identification tag, or a magnetic or radioactive material and the cavity may be machined at or near the center of said end surface.

The invention also relates to a string of joined tubulars that are marked in accordance with the invention, so that a marker is permanently arranged in a cavity adjacent to at least one joined tubular joint. The tubular string may comprise a plurality of joints that are provided with markers, wherein each marker transmits a radio, magnetic, radioactive or other detectable signal, which is detected using appropriate equipment, and may be different to the signal transmitted by any other marker.

Thus, the present invention provides an improved method of marking joint locations when used with screw thread connections or welding techniques, such as forge welding, fusion welding, diffusion welding, amorphous bonding, friction welding or other techniques in which a metallurgical bond is formed between abutted pipe ends. It preferably involves positioning a marker mid-wall in a tubular joint such that it is an integral part of the joint and cannot be dislodged.

Figure 27:
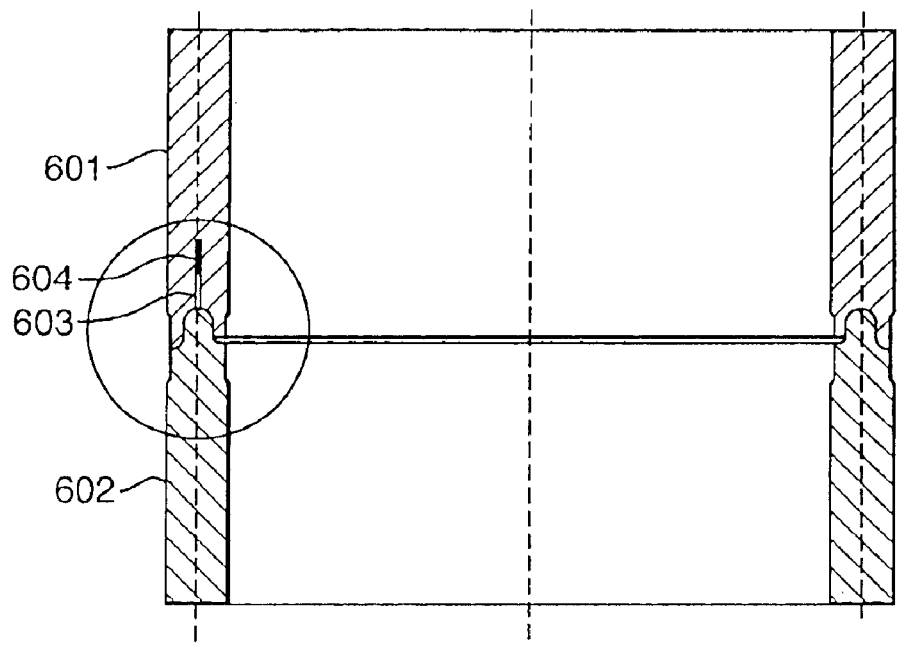
FIG. 27 is a longitudinal sectional view of prepared and mated ends of pipe joints suitable for welding in which a marker has been inserted in accordance with the method according to the invention.
Figure 28:
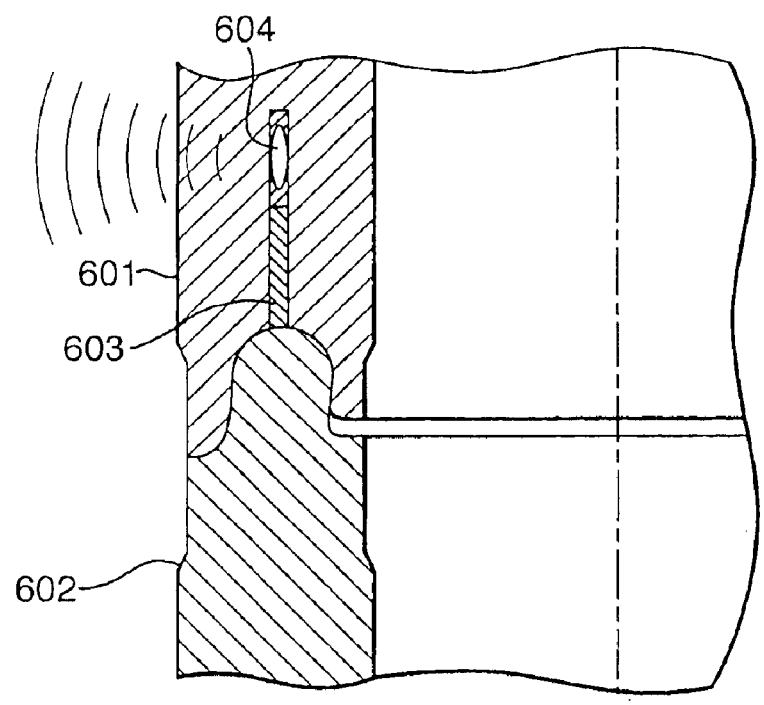
FIG. 28 is an enlarged longitudinal section view of the prepared and mated ends and marker shown in FIG. 27.

As shown in FIGS. 27 and 28 the method according to the invention involves preparing the tubular ends 601 and 602 of a tubular joint for welding, and machining a slot or hole 603 into an end face of one of the tubular ends 601.

A small electronic tag, or amount of radioactive or magnetic material may then be placed securely into the slot 603 to act as a permanent marker 604. When welding takes place the area containing the marker is forged and the marker 604 becomes trapped inside the made-up string of pipes, which are lowered into the hole. When necessary it may then be detected using an appropriate logging device.

Figure 29:
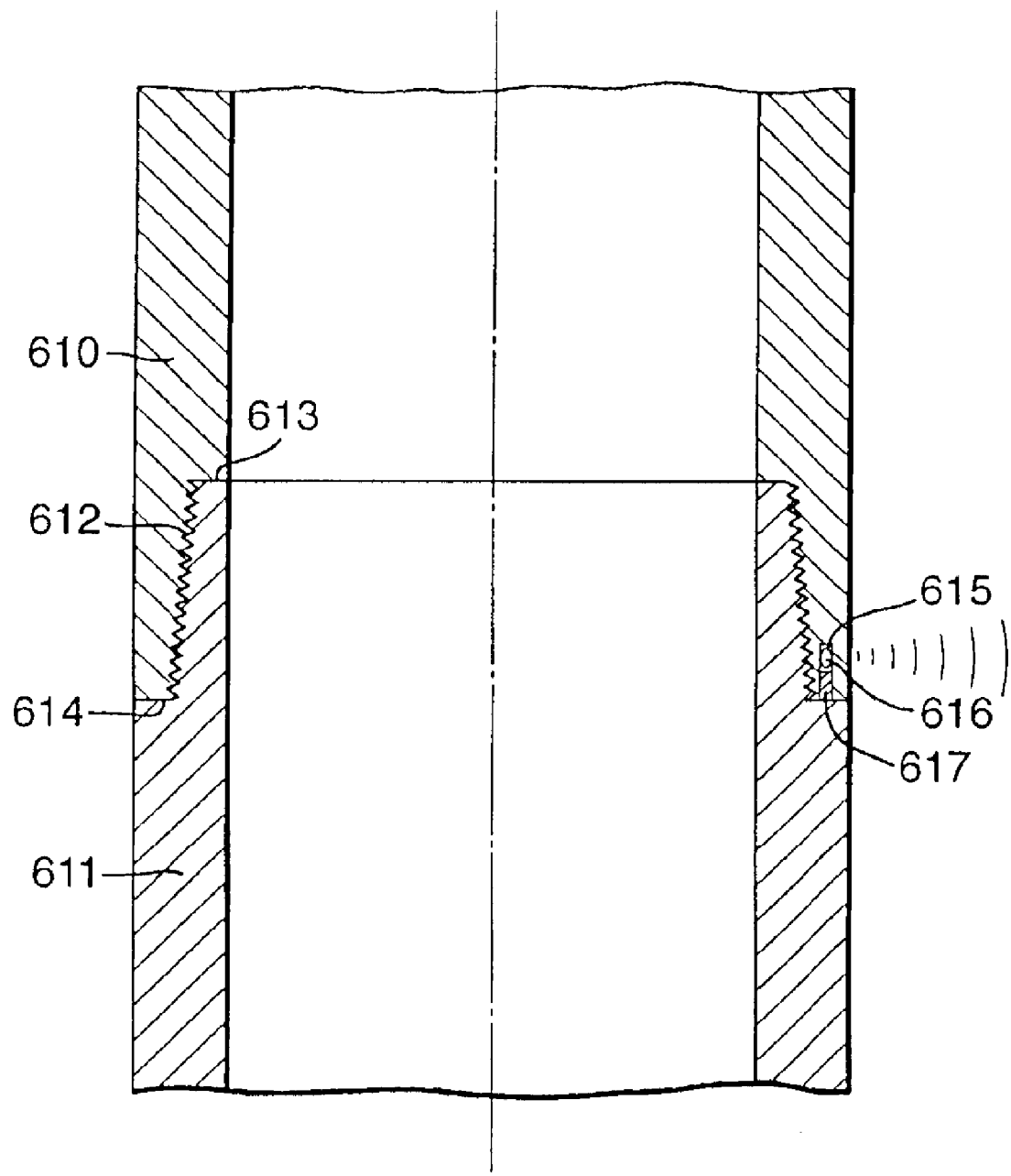
FIG. 29 is a longitudinal sectional view of a pair of tubulars that are interconnected by a screw thread connector and an end surface of one tubular comprises a cavity in which a marker is inserted.

FIG. 29 depicts an embodiment of the joint marking method according to the invention wherein a pair of tubulars 610, 611 is interconnected by a screw thread connector 612 such that inner and outer disk-shaped end surfaces 613 and 614 are pressed together after the screw thread connection has been made.

A cavity 615 has been drilled into the outer disk-shaped end face of the upper tubular 610, in which cavity 615 a marker 616 has been-inserted. The marker 616 is embedded in a sealant 617 that seals off the entrance of the cavity.

The marker 616 is adequately sealed off from fluids in the interior and exterior of the string of tubulars 610, 611 and is adequately protected from impacts and forces exerted on the inner and outer walls of the string of tubulars 610, 611.

We claim:

1. A method for inspecting welds between welded tubular ends, the method comprising the steps of:

arranging a series of electromagnetic acoustic transducer (EMAT) assemblies in circumferential direction adjacent to an inner and/or outer surface of at least one of the welded tubular ends; and inducing the EMAT assemblies to transmit sequentially or simultaneously acoustic shear wave signals in different modes and angles towards the weld and to detect the shear waves reflected by and/or passing through the weld such that at least a substantial part of the weld is scanned by the EMAT assemblies; wherein the EMAT assemblies are maintained at a substantially fixed position relative to the weld during the scanning operation.

2. The method of claim 1, wherein the EMAT assemblies comprise a ring shaped assembly of EMAT transmitters and a ring shaped assembly of EMAT receivers, which is arranged between the weld and the ring shaped assembly of EMAT transmitters.

3. The method of claim 2, wherein the EMAT assemblies comprise ring shaped assemblies of EMAT transmitter and receiver assemblies at both sides of the weld when seen in longitudinal direction of the welded tubulars.

4. The method of claim 2, wherein each of the EMAT transmitter and receiver assemblies comprises a matrix of EMAT transducers which at least partly overlap each other in a circumferential direction.

5. The method of claim 4, wherein the EMAT transducers of at least one matrix are stacked on top of each other in a partially overlapping pattern in a radial direction relative to the tube wall.

6. The method of claim 4, wherein the EMAT transducers of at least one matrix are staggered in a substantially longitudinal direction relative to the tube wall.

7. The method of any preceding claim wherein the EMAT assembly is arranged on a carrier body that is arranged in the interior of at least one of the welded tubulars.

8. The method of claim 1, wherein the EMAT assemblies are arranged on a carrier sleeve which surrounds at least one of the welded tubulars and which can optionally be split into at least two sleeve segments after completion of the welding operation.

9. The method of claim 1, wherein the EMAT assemblies are operated to inspect the quality of forge welded tubulars instantly after the forge weld has been made.

10. An EMAT assembly for inspecting welds between welded tubular ends, the assembly comprising;

a series electromagnetic acoustic transducers which are in use distributed in a circumferential direction adjacent to an inner and/or outer surface of at least one of the welded tubular ends and are configured to transmit sequentially or simultaneously acoustic shear wave signals in different modes and angles towards the weld and to detect the shear waves reflected by and/or passing through the weld such that at least a substantial part of the weld is scanned by the EMAT assembly.

11. The EMAT assembly of claim 10, wherein the assembly comprises at least two longitudinally spaced ring shaped arrays of EMAT transmitters and receivers and wherein the ring shaped arrays of EMAT receivers are located between the ring shaped arrays of EMAT transmitters.

* * * * *